United States Patent
During

(10) Patent No.: US 11,918,551 B2
(45) Date of Patent: Mar. 5, 2024

(54) METHODS OF TREATING SEIZURE DISORDERS AND PRADER-WILLI SYNDROME

(71) Applicant: Ovid Therapeutics, Inc., New York, NY (US)

(72) Inventor: Matthew During, Darien, CT (US)

(73) Assignee: OVID THERAPEUTICS INC., New York, NY (US)

( * ) Notice: Subject to any disclaimer, the term of this patent is extended or adjusted under 35 U.S.C. 154(b) by 271 days.

(21) Appl. No.: 17/322,853

(22) Filed: May 17, 2021

(65) Prior Publication Data

US 2023/0149332 A1    May 18, 2023

Related U.S. Application Data

(63) Continuation of application No. 16/484,595, filed as application No. PCT/US2018/017382 on Feb. 8, 2018, now abandoned.

(60) Provisional application No. 62/456,320, filed on Feb. 8, 2017.

(51) Int. Cl.
 *A61K 31/196* (2006.01)
 *A61P 25/08* (2006.01)

(52) U.S. Cl.
 CPC ........... *A61K 31/196* (2013.01); *A61P 25/08* (2018.01)

(58) Field of Classification Search
 CPC .............................. A61K 31/196; A61P 25/08
 See application file for complete search history.

(56) References Cited

U.S. PATENT DOCUMENTS

| | | | |
|---|---|---|---|
| 6,794,413 B1 | 9/2004 | Silverman et al. | |
| 8,969,413 B2 | 3/2015 | Silverman et al. | |
| 9,670,141 B2 | 6/2017 | Silverman et al. | |
| 9,993,449 B2 | 6/2018 | Silverman et al. | |
| 2009/0209937 A1 | 8/2009 | Rogawski et al. | |
| 2012/0283323 A1 | 11/2012 | Silva et al. | |
| 2013/0041028 A1 | 2/2013 | Silverman et al. | |
| 2014/0303243 A1 | 10/2014 | Hakonarson et al. | |
| 2015/0224164 A1 | 8/2015 | Glass et al. | |
| 2017/0101364 A1 | 4/2017 | Silverman et al. | |
| 2017/0239202 A1* | 8/2017 | Silverman | A61P 25/06 |
| 2018/0271816 A1 | 9/2018 | Silverman et al. | |

FOREIGN PATENT DOCUMENTS

| | | |
|---|---|---|
| WO | 2008023364 A1 | 2/2008 |
| WO | 2017062942 A2 | 4/2017 |

OTHER PUBLICATIONS

Chiron (Epilepsy Research vol. 26 pp. 389-395 published 1997) (Year: 1997).*
Doumlele (Epilepsy and Behavior Case Reports vol. 6 pp. 67-69 published 2016). (Year: 2016).*
English translation of Israeli Office Action dated Nov. 16, 2021, corresponding to counterpart Israeli Application No. 268212; 3 pages.
Japanese Office Action (English Summary) dated Nov. 24, 2021, corresponding to counterpart Japanese Application No. 2019-563351; 1 page.
Lippert, et al., "4-Amino-hex-5-enoic Acid, a Selective Catalytic Inhibitor of 4-Aminobutyric-Acid Aminotransferase in Mammalian Brain", Eur. J. Biochem,vol. 74, No. 3; Apr. 15, 1977; pp. 441-445.
Dewey et al., "A Novel Strategy for the Treatment of Cocaine Addiction", Synapse, vol. 30, No. 2, Oct. 1998; pp. 119-129.
Dewey et al., "A Pharmacologic Strategy for the Treatment of Nicotine Addiction", Synapse, vol. 31, No. 1, Jan. 1999; pp. 76-86.
Gerasimov et al., "Gamma-Vinyl GABA Inhibits Methamphetamine, Heroin, or Ethanol-Induced Increases in Nucleus Accumbens Dopamine", Synapse, vol. 34, No. 1, Oct. 1999; pp. 11-19.
Pan et al., "Design, Synthesis, and Biological Activity of a Difluoro-Substituted, Conformationally Rigid Vigabatrin Analogue as a Potent ?-Aminobutyric Acid Aminotransferase Inhibitor", Journal of Medicinal Chemistry, vol. 46, No. 25, Dec. 4, 2003;pp. 5292-5293.
International Search Report and Written Opinion of the International Searching Authority, corresponding to International Application No. PCT/US2016/056245, dated Jan. 26, 2017; 16 total pages.

(Continued)

*Primary Examiner* — Theodore R. Howell
*Assistant Examiner* — George W Kosturko
(74) *Attorney, Agent, or Firm* — Carter, DeLuca & Farrell LLP

(57) ABSTRACT

Methods of treating a seizure disorder with (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, are provided. The methods provide therapeutic compositions that may be used to improve one or more symptoms of a seizure disorder. Methods of treating Prader-Willi syndrome with (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, are provided. The methods provide therapeutic compositions that may be used to improve one or more symptoms of Prader-Willi syndrome.

7 Claims, No Drawings

(56) References Cited

OTHER PUBLICATIONS

Lu, et al., "Fluorinated Conformationally-Restricted ?-Aminobutyric Acid Aminotransferase Inhibitors", Journal of Medicinal Chemistry, E-Pub, vol. 49, No. 25, Oct. 11, 2006; pp. 7404-7412 and Figures 1-2.

Kanth et al., "QSAR Analysis of a Few GABA Aminotransferase Inhibitors as Potent Antiepileptics", Indian Journal of Chemistry, vol. 44B, Mar. 2005; pp. 595-599.

Chebib et al., "The Effects of Cyclopentane and Cyclopentene Analogues of GABA at Recombinant GABAC Receptors", European Journal of Pharmacology, vol. 430, No. 2-3; Nov. 2001; pp. 185-192.

Notification concerning Transmittal of International Preliminary Report on Patentability (Chapter I of the Patent cooperation Treaty), dated Apr. 19, 2018, including International Preliminary Report on Patentability and Written Opinion International Search Report and Written Opinion of the International Searching Authority, corresponding to International Application No. PCT/US2016/056245; 13 total pages.

Tolman et al., "Treatment options for refractory and difficult to treat seizures: focus on vigabatrin", (Dovepress) Therapeutics and Clinical Risk Management, 2011, vol. 7; pp. 367-375.

Jozwiak et al., "Antiepileptic treatment before the onset of seizures reduces epilepsy severity and risk of mental retardation in infants with tuberous sclerosis complex", (Elsevier) Official Journal of the European Pediatric Neurology Society, European Journal of Pediatric Neurology 15 (2011); pp. 424-431.

Aycan et al., "Prader-Willi Syndrome and Growth Hormone Deficiency", J. Clin Res Pediatr. Endocrinol 2014, vol. 6, No. 2; pp. 62-67.

Han et al., "Lower Brain-Derived Neurotrophic Factor in Patients with Prader-Willi Syndrome Compared to Obese and Lean Control Subjects", J. Clin. Endo. Metab. (2010), vol. 95; pp. 3532-3536.

Cao et al., "Molecular therapy of obesity and diabetes using a physiological autoregulatory approach", Nat. Med., Apr. 2009, vol. 15, No. 4; pp. 447-454.

Carrel et al., "Long-Term Growth Hormone Therapy Changes the Natural History of Body Composition and Motor Function in Children with Prader-Willi Syndrome", J Clin Endocrinol Metab., Mar. 2010, vol. 95, No. 3, pp. 1131-1136.

Blume et al., ILAE Commission Report, Glossary of Descriptive Terminology for Ictal Semiology: Report of the ILAE Task Force on Classification and Terminology, Blackwell Science, Inc., International League Against Epilepsy, Epilepsia, (2001), vol. 42, No. 9; pp. 1212-1218.

International Search Report and Written Opinion, dated Apr. 16, 2018, corresponding to International Application No. PCT/US2018/017382; 8 pages.

Fuchs et al., "Inhibition of GSK3ß rescues hippocampal development and learning in a mouse model of CDKL5 disorder", Neurobiology of Disease, (2015), vol. 82, pp. 298-310.

Richard B. Silverman, "The 2011 E.B. Hershberg Award for Important Discoveries in Medicinally Active Substances: (1S, 3S)-3-Amino-4-difluoromethylenyl-1-cyclopentanoic Acid (CPP-115), a GABA Aminotransferase Inactivator and New Treatment for Drug Addiction and Infantile Spasms," Journal of Medicinal Chemistry, (2012); vol. 55; pp. 567-575.

Doumlele et al., "A case report on the efficacy of vigabatrin analogue (1S, 3S)-3-amino-4-difluoromethylenyl-1-cyclopentanoic acid (CPP-115) in a patient with infantile spasms," Epilepsy & Behavior Case Reports, vol. 6, (2016); pp. 67-69.

Muller et al, "Retrospective evaluation of low long-term efficacy of antiepileptic drugs and ketogenic diet in 39 patients with CDKL5-related epilepsy," Official Journal of the European Paediatric Neurology Society, vol. 20, (2016); pp. 147-151.

European Search Report dated Oct. 15, 2020, corresponding to counterpart European Application No. 18752026.7; 9 pages.

Moseley et al., "Historic Clinical, and Prognostic Features of Epileptic Encephalopathies Caused by CDKL5 Mutations," Pediatric Neurology 46, (2012); pp. 101-105.

Juncosa et al., "Design and Mechanism of (S)-3-Amino-4-(difluoromethylenyl)cyclopent-1-ene-1-carboxylic Acid, a Highly Potent y-Aminobutyric Acid Aminotrnsferase Inactivator for the Treatment of Addiction," Journal of the American Chemical Society, vol. 140, 2018; pp. 2151-2164.

Pan et al., "CPP-115, a Potent y-Aminobutyric Acid Aminotransferase Inactivator for the Treatment of Cocaine Addiction," J. Med. Chem, vol. 55, No. 1, Jan. 12, 2012; pp. 357-366.

Australian Examination Report dated Mar. 18, 2021, corresponding to counterpart Australian application No. 2018219861; 4 pages.

Dech et al., "The Use of Fluoxetine in an Adolescent with Prader-Willi Syndrome," J. Am. Acad. Child Adolesc. Psychiatry, vol. 30, Mar. 1991; pp. 298-302.

Selikowitz et al., "Fenfluramine in Prader-Willi syndrome: a double blind, placebo controlled trial," Archives of Disease in Childhood, vol. 65, (1990); pp. 112-114.

Itoh et al., "Effects of Mazindol in Two Patients With Prader-Willi Syndrome," Pediatric Neurology, vol. 13, No. 4, (1995); pp. 349-351.

Smathers, et al., "Topiramate Effectiveness in Prader-Willi Syndrome," Pediatric Neurology, vol. 28, No. 2, (2003); pp. 130-132.

Archer. H L, et al. "CDKL5 mutations cause infantile spasms, early onset seizures, and severe mental retardation in female patients," Journal of medical genetics, Sep. 2006, pp. 729-734, 43.9.

Briggs, Stephen W., et al. "CPP-115, a vigabatrin analogue, decreases spasms in the multiple-hit rat model of infantile spasms," Epilepsia, Jan. 2014, pp. 94-102, 55.1.

Chinese Office Action dated Jun. 1, 2022, corresponding to counterpart Chinese Application No. 201880022399X; 7 pages.

Japanese Office Action (English Summary) dated Jul. 12, 2022, corresponding to counterpart Japanese Application No. 2019-563351; 1 page.

\* cited by examiner

METHODS OF TREATING SEIZURE DISORDERS AND PRADER-WILLI SYNDROME

CROSS REFERENCE TO RELATED APPLICATION

This application is a continuation application of U.S. patent application Ser. No. 16/484,595, filed Aug. 8, 2019, which a U.S. National Stage entry of International Application No. PCT/US2018/017382, filed on Feb. 8, 2018, which claims benefit of and priority to U.S. Provisional Application No. 62/456,320, filed Feb. 8, 2017, the disclosures of each of which are hereby incorporated by reference herein in their entirety.

TECHNICAL FIELD

Methods of treating seizure disorders and Prader-Willi syndrome are provided.

BACKGROUND

Seizure disorders typically involve abnormal nerve cell activity in the brain, causing seizures which may be manifested by periods of unusual behavior, sensations, convulsions, diminished consciousness and sometimes loss of consciousness. Seizures can be a symptom of many different disorders that can affect the brain. Epilepsy is a seizure disorder characterized by recurrent seizures. See, e.g., Blume et al., Epilepsia. 2001; 42:1212-1218. Epileptic seizures are usually marked by abnormal electrical discharges in the brain and typically manifested by sudden brief episodes of altered or diminished consciousness, involuntary movements, or convulsions. Abnormal electrical activity in the brain may be measured or detected by electroencephalography (EEG). Clinical epileptic seizures can be preceded by abnormal electrical activity detected in EEG recordings as multifocal spikes which provide evidence of epileptic discharges but are not accompanied by seizures. See, e.g., Jóźwiak et al., European Journal of Paediatric Neurology, 2011, 15(5) 424-431 ("Jóźwiak et al"). Non-epileptic seizures may or may not be accompanied by abnormal electrical activity in the brain and may be caused by psychological issues or stress. Drug or alcohol withdrawal can also cause seizures. Seizure symptoms can vary widely. Some seizures can hardly be noticed, while others are totally disabling. Seizure disorders include epilepsy.

Hamartomas may be associated with certain seizure disorders. Hamartomas are a mostly benign, focal malformation that resembles a neoplasm in the tissue of its origin. They are composed of tissue elements normally found at that site, but grow in a disorganized manner. Hamartomas can originate in the brain. Tuberous Sclerosis Complex (TSC) is a genetic seizure disorder characterized by hamartomatous growth in various organs. The earliest symptoms of TSC can include heart tumors and cortical tubers, which can be seen even prenatally. Patients who have this disorder can exhibit a high rate of epilepsy and cognitive problems resulting from multiple lesions in the brain. TSC lesions (corticol tubers) typically contain dysmorphic neurons, brightly eosinophilic giant cells and white matter alterations. Seizures associated with TSC can be intractable. Tuber cinereum hamartoma (also known as hypothalamic hamartoma) is a benign tumor in which a disorganized collection of neurons and glia accumulate at the tuber cinereum of the hypothalamus. Symptoms include gelastic seizures, a disorder characterized by spells of involuntary laughter with interval irritability and depressed mood. Antiepileptic treatment before the onset of seizures can reduce epilepsy severity and the risk of mental retardation in infants with TSC. See, e.g., Jóźwiak et al.

Infantile spasms (IS) is a specific type of seizure disorder seen in infancy and childhood and is also known as West Syndrome, juvenile spasms or epileptic spasms. West Syndrome is characterized by infantile spasms, developmental regression, and a specific pattern on EEG testing called hypsarrhythmia (chaotic brain waves). The onset of infantile spasms is usually in the first year of life, typically between 3-12 months, typically manifesting around the fifth month. The seizures primarily consist of a sudden bending forward of the body with stiffening of the arms and legs; some children arch their backs as they extend their arms and legs. Spasms tend to occur upon awakening or after feeding, and often occur in clusters of up to 100 spasms at a time. Infants may have dozens of clusters and several hundred spasms per day. Infantile spasms usually stop by mid-childhood, but may be replaced by other seizure types. The intellectual prognosis for children with infantile spasm is generally poor. Treatment with corticosteroids such as prednisone is standard, although serious side effects can occur. Several antiepileptic medications, such as topiramate may ease some symptoms. Vigabatrin been approved by the U.S. Food and Drug Administration to treat infantile spasms in children ages one month to two years.

Lennox-Gastaut syndrome (LGS) is a severe seizure disorder. Seizures usually begin before 4 years of age. Seizure types, which vary among patients, include tonic (stiffening of the body, upward deviation of the eyes, dilation of the pupils, and altered respiratory patterns), atonic (brief loss of muscle tone and consciousness, causing abrupt falls), atypical absence (staring spells), and myoclonic (sudden muscle jerks). There may be periods of frequent seizures mixed with brief, relatively seizure-free periods. Many children with Lennox-Gastaut syndrome typically experience some degree of impaired intellectual functioning or information processing, along with developmental delays, and behavioral disturbances. Lennox-Gastaut syndrome can be caused by brain malformations, perinatal asphyxia, severe head injury, central nervous system infection and inherited degenerative or metabolic conditions. In certain cases, no cause can be found. Treatment for Lennox-Gastaut syndrome includes clobazam and anti-epileptic medications such as valproate, lamotrigine, felbamate, or topiramate. There is usually no single antiepileptic medication that will completely control seizures. Children who improve initially may later show tolerance to a drug or have uncontrollable seizures.

CDKL5 disorder is an X-linked genetic seizure disorder that results in severe neurodevelopmental impairment and early onset, difficult to control seizures. CDKL5 stands for cyclin-dependent kinase-like 5, and is a gene located on the X chromosome. The CDKL5 gene was previously called STK9. Although CDKL5 disorder is primarily associated with females, it has been seen in males as well. A predominant characteristic associated with CDKL5 mutations is the so-called epileptic encephalopathy, the onset of severe seizures in the first six months of life (often within the first 3 months), and poor subsequent neurocognitive development and commonly the presence of repetitive hand movements (stereotypies). Most afflicted children cannot walk, talk or feed themselves, and many are confined wheelchairs, dependent on others for everything. Many also suffer with scoliosis, visual impairment, sensory issues and various gastrointestinal difficulties. Other symptoms of a CDKL5 disorder often include: low or poor muscle tone, hand wringing movements or mouthing of the hands, marked developmental delay, limited or absent speech, lack of eye contact or poor eye contact, gastroesophageal reflux, constipation, small, cold feet, breathing irregularities such as hyperventilation, grinding of the teeth, episodes of laughing or crying for no reason, very limited hand skills, some autistic-like tendencies, scoliosis, cortical visual impairment (CVI), aka "cortical blindness", apraxia, eating/drinking challenges, sleep difficulties, characteristics such as a sideways glance, and a habit of leg crossing. There are currently no approved drugs to treat CDKL5 disorder. Seizure control is challenging, and is often the most difficult health issue to manage. No one antiepileptic drug has been found to be uniformly effective, and often multiple anticonvulsants are needed.

Medications are used to treat seizure disorders and can be referred to as anti-epileptic drugs ("AED"). The treatment of recurrent seizures predominantly centers on the utilization of at least one AED, with possible adjunctive use of a second or even third agent in the case of monotherapeutic failure. See, Tolman and Faulkner, Ther Clin Risk Manag. 2011; 7:367-375. However, approximately 30%-40% of epileptic patients have inadequate seizure control with just one AED, and require the use of adjunctive agents. Id. A subset of this group will have regular and persistent seizure activity despite reasonable doses of multiple AEDs. These seizures are considered refractory to treatment. Id. Accordingly, there remains a need for improved and/or additional therapies for treating seizure disorders.

Prader-Willi syndrome (PWS) is a genetic disease caused by lack of expression of genes from an imprinted region of the paternally inherited chromosome 15q11-q13, near the centromere (Aycan and Bas, *J Clin Res Pediatr Endocrinol*, 6(2):62-67 (2014)). The frequency of the disease is between about 1/10,000 and 1/30,000 with approximately 400,000 PWS patients living worldwide. PWS is a spectrum disorder which affects many systems in the body. Subjects with PWS typically suffer from a host of symptoms including neurologic, cognitive, endocrine, and behavioral abnormalities. Initially, infants exhibit hypotonia (floppy baby syndrome) and experience difficulty in sucking and feeding which can lead to growth delay. Subjects with PWS frequently have poor muscle tone, growth hormone deficiency, low levels of sex hormones, a constant feeling of hunger and excessive appetite (hyperphagia). They overeat, leading to weight gain, obesity and a high incidence of diabetes. Other signs appear including short stature, poor motor skills, underdeveloped sex organs, and mild intellectual and learning disabilities. PWS subjects may experience delayed speech and language development, and infertility. Behavioral symptoms may include cognitive impairment, cognitive rigidity, emotional lability and obsessive-compulsive behavior, with autistic symptomology, psychotic episodes, and biopolar disorder with psychosis. Additional clinical manifestations may include excessive daytime sleepiness, scoliosis, osteopenia/osteoporosis, decreased gastrointestinal motility, sleep disturbances, and reduced pain sensitivity.

PWS is the most common genetic neurodevelopmental disorder associated with obesity. Data indicates that PWS is associated with an approximate 50% reduction in plasma BDNF levels normalized to body weight (Han et al., *J. Clin. Endo. Metab.*, 95, 3532-36 (2010)). Studies also show that selectively up-regulating BDNF in the hypothalamus inhibits appetite and weight gain in mice on a high fat diet, and at very high levels of expression using viral vector gene transfer causes severe weight loss in normal control chow fed mice (Cao, et al., *Nat Med.*, 15(4):447-54 (2009)). BDNF appears to act downstream to other modulators of feeding, notably leptin and the MC4 receptor.

There is currently no cure for PWS. Growth hormone, exercise, and dietary supervision can help build muscle mass and control weight. Treatment with human growth hormone starting by 2 years of age has been reported to improve body composition, motor function, height, and lipid profiles. See, Carrel et al., *J Clin Endocrinol Metab.*, 95(3):1131-1136 (2010 March). Other treatments may include oxytocin, sex hormones and behavior therapy. However, most people with PWS will need specialized care and supervision throughout their lives. There remains a need for improved and/or additional therapies for treating PWS.

SUMMARY

Methods of treating a seizure disorder are provided and, in embodiments, include administering to a subject in need thereof an effective amount of (1S,3S)-3-amino-4-(difluoromethylidene)cyclopentane-1-carboxylic acid or a pharmaceutically acceptable salt thereof. In embodiments, methods of treating a seizure disorder include administering (1S,3S)-3-amino-4-(difluoromethylidene)cyclopentane-1-carboxylic acid or a pharmaceutically acceptable salt thereof to a subject in need thereof to provide improvement in one or more symptoms of the disorder. In embodiments, methods of treating a seizure disorder include administering (1S,3S)-3-amino-4-(difluoromethylidene)cyclopentane-1-carboxylic acid or a pharmaceutically acceptable salt thereof to a subject in need thereof to provide improvement in next day functioning of the subject. In embodiments, methods of treating a seizure disorder include administering (1S,3S)-3-amino-4-(difluoromethylidene)cyclopentane-1-carboxylic acid or a pharmaceutically acceptable salt thereof to a subject in need thereof prior to the onset of clinical seizures after detection of abnormal EEG to reduce or prevent symptoms of the seizure disorder. In embodiments, methods of treating an abnormal EEG signature include administering (1S,3S)-3-amino-4-(difluoromethylidene)cyclopentane-1-carboxylic acid or a pharmaceutically acceptable salt thereof to a subject having the abnormal EEG signature.

In embodiments, methods of treating a seizure disorder include administering to a subject in need thereof an effective amount of (S)-3-amino-4-(difluoromethylenyl)cyclopent-1-ene-1-carboxylic acid or a pharmaceutically acceptable salt thereof. In embodiments, methods of treating a seizure disorder include administering (S)-3-amino-4-(difluoromethylenyl)cyclopent-1-ene-1-carboxylic acid or a pharmaceutically acceptable salt thereof to a subject in need thereof to provide improvement in one or more symptoms of the disorder. In embodiments, methods of treating a seizure disorder include administering (S)-3-amino-4-(difluoromethylenyl)cyclopent-1-ene-1-carboxylic acid or a pharmaceutically acceptable salt thereof to a subject in need thereof to provide improvement in next day functioning of the subject. In embodiments, methods of treating a seizure disorder include administering (S)-3-amino-4-(difluoromethylenyl)cyclopent-1-ene-1-carboxylic acid or a pharmaceutically acceptable salt thereof to a subject in need thereof prior to the onset of clinical seizures after detection of abnormal EEG to reduce or prevent symptoms of the seizure disorder. In embodiments, methods of treating an abnormal EEG signature include administering (S)-3-amino-4-(difluoromethylenyl)cyclopent-1-ene-1-carboxylic acid or a pharmaceutically acceptable salt thereof to a subject having the abnormal EEG signature.

In embodiments, methods of treating a seizure disorder include administering (1S,3S)-3-amino-4-(difluoromethylidene)cyclopentane-1-carboxylic acid or a pharmaceutically acceptable salt thereof, in combination with (S)-3-amino-4-(difluoromethylenyl)cyclopent-1-ene-1-carboxylic acid or a pharmaceutically acceptable salt thereof, to a subject in need thereof.

In embodiments, the seizure disorders include epilepsy, epilepsy with generalized tonic-clonic seizures, epilepsy with myoclonic absences, frontal lobe epilepsy, temporal lobe epilepsy, Landau-Kleffner Syndrome, Dravet syndrome, Rasmussen's syndrome, Doose syndrome, CDKL5 disorder, infantile spasms (West syndrome), Lennox-Gastaut syndrome (LGS), Rett syndrome, Ohtahara syndrome, CDKL5 disorder, childhood absence epilepsy, essential tremor, and acute repetitive seizures, benign rolandic epilepsy, status epilepticus, refractory status epilepticus, super-refractory status epilepticus (SRSE), PCDH19 pediatric epilepsy, drug withdrawal induced seizures, alcohol withdrawal induced seizures, and increased seizure activity or breakthrough seizures (increased seizure activity; also called serial or cluster seizures). In embodiments, the seizure disorder is status epilepticus.

Methods of treating Prader-Willi syndrome are provided and, in embodiments, include administering to a subject in need thereof an effective amount of (1S,3S)-3-amino-4-(difluoromethylidene)cyclopentane-1-carboxylic acid or a pharmaceutically acceptable salt thereof. In embodiments, methods of treating Prader-Willi syndrome include administering (1S,3S)-3-amino-4-(difluoromethylidene)cyclopentane-1-carboxylic acid or a pharmaceutically acceptable salt thereof to a subject in need thereof to provide improvement in one or more symptoms of the syndrome. In embodiments, methods of treating Prader-Willi syndrome include administering (1S,3S)-3-amino-4-(difluoromethylidene)cyclopentane-1-carboxylic acid or a pharmaceutically acceptable salt thereof to a subject in need thereof to provide improvement in next day functioning of the subject. In embodiments, methods of treating Prader-Willi syndrome include administering to a subject in need thereof an effective amount of (S)-3-amino-4-(difluoromethylenyl)cyclopent-1-ene-1-carboxylic acid or a pharmaceutically acceptable salt thereof. In embodiments, methods of treating Prader-Willi Syndrome include administering (S)-3-amino-4-(difluoromethylenyl)cyclopent-1-ene-1-carboxylic acid or a pharmaceutically acceptable salt thereof to a subject in need thereof to provide improvement in one or more symptoms of the syndrome. In embodiments, methods of treating Prader-Willi Syndrome include administering (S)-3-amino-4-(difluoromethylenyl)cyclopent-1-ene carboxylic acid or a pharmaceutically acceptable salt thereof to a subject in need thereof to provide improvement in next day functioning of the subject. In embodiments, methods of treating Prader-Willi syndrome include administering (1S,3S)-3-amino-4-(difluoromethylidene)cyclopentane carboxylic acid or a pharmaceutically acceptable salt thereof, in combination with (S)-3-amino (difluoromethylenyl)cyclopent-1-ene-1-carboxylic acid or a pharmaceutically acceptable salt thereof, to a subject in need thereof.

DETAILED DESCRIPTION

Methods of treating a seizure disorder are provided and, in embodiments, include administering to a subject in need thereof an effective amount of (1S,3S)-3-amino-4-(difluoromethylidene)cyclopentane-1-carboxylic acid or a pharmaceutically acceptable salt thereof. In embodiments, methods of treating a seizure disorder include administering (1S,3S)-3-amino-4-(difluoromethylidene)cyclopentane-1-carboxylic acid or a pharmaceutically acceptable salt thereof to a subject in need thereof to provide improvement in one or more symptoms of the disorder. In embodiments, methods of treating a seizure disorder include administering (1S,3S)-3-amino-4-(difluoromethylidene)cyclopentane-1-carboxylic acid or a pharmaceutically acceptable salt thereof to a subject in need thereof to provide improvement in next day functioning of the subject. In embodiments, methods of treating a seizure disorder include administering (1S,3S)-3-amino-4-(difluoromethylidene)cyclopentane-1-carboxylic acid or a pharmaceutically acceptable salt thereof to a subject in need thereof prior to the onset of clinical seizures after detection of abnormal EEG to reduce or prevent symptoms of the seizure disorder. In embodiments, methods of treating an abnormal EEG signature include administering (1S,3S)-3-amino-4-(difluoromethylidene)cyclopentane-1-carboxylic acid or a pharmaceutically acceptable salt thereof to a subject having the abnormal EEG signature.

In embodiments, methods of treating a seizure disorder include administering to a subject in need thereof an effective amount of (S)-3-amino-4-(difluoromethylenyl)cyclopent-1-ene-1-carboxylic acid or a pharmaceutically acceptable salt thereof. In embodiments, methods of treating a seizure disorder include administering (S)-3-amino-4-(difluoromethylenyl)cyclopent-1-ene-1-carboxylic acid or a pharmaceutically acceptable salt thereof to a subject in need thereof to provide improvement in one or more symptoms of the disorder. In embodiments, methods of treating a seizure disorder include administering (S)-3-amino-4-(difluoromethylenyl)cyclopent-1-ene-1-carboxylic acid or a pharmaceutically acceptable salt thereof to a subject in need thereof to provide improvement in next day functioning of the subject. In embodiments, methods of treating a seizure disorder include administering (S)-3-amino-4-(difluoromethylenyl)cyclopent-1-ene-1-carboxylic acid or a pharmaceutically acceptable salt thereof to a subject in need thereof prior to the onset of clinical seizures after detection of abnormal EEG to reduce or prevent symptoms of the seizure disorder. In embodiments, methods of treating an abnormal EEG signature include administering (S)-3-amino-4-(difluoromethylenyl)cyclopent-1-ene-1-carboxylic acid or a pharmaceutically acceptable salt thereof to a subject having the abnormal EEG signature.

In embodiments, methods of treating a seizure disorder include administering (1S,3S)-3-amino-4-(difluoromethylidene)cyclopentane-1-carboxylic acid or a pharmaceutically acceptable salt thereof, in combination with (S)-3-amino-4-(difluoromethylenyl)cyclopent-1-ene-1-carboxylic acid or a pharmaceutically acceptable salt thereof, to a subject in need thereof.

Examples of seizure disorders include epilepsy, epilepsy with generalized tonic-clonic seizures, epilepsy with myoclonic absences, frontal lobe epilepsy, temporal lobe epilepsy, Landau-Kleffner Syndrome, Rasmussen's syndrome, Dravet syndrome, Doose syndrome, CDKL5 disorder, infantile spasms (West syndrome), juvenile myoclonic epilepsy (JME), vaccine-related encephalopathy, intractable childhood epilepsy (ICE), Lennox-Gastaut syndrome (LGS), Rett syndrome, Ohtahara syndrome, CDKL5 disorder, childhood absence epilepsy, essential tremor, acute repetitive seizures, benign rolandic epilepsy, status epilepticus, refractory status epilepticus, super-refractory status epilepticus (SRSE), PCDH19 pediatric epilepsy, drug withdrawal induced seizures, alcohol withdrawal induced seizures, increased seizure activity or breakthrough seizures (also called serial or cluster seizures). In embodiments, the seizure disorder is associated with a sodium channel protein type 1 subunit alpha (Scn1a)-related disorder.

In embodiments, the seizure disorder is status epilepticus (SE). SE is characterized by an epileptic seizure of greater than five minutes or more than one seizure within a five-minute period without the person returning to normal between them. SE can be a dangerous condition that can lead to mortality if treatment is delayed. SE can be convulsive, with a regular pattern of contraction and extension of the arms and legs, or non-convulsive, with a change in a person's level of consciousness of relatively long duration but without large scale bending and extension of the limbs due to seizure activity. Convulsive SE (CSE) may be further classified into (a) tonic-clonic SE, (b) tonic SE, (c) clonic SE and (d) myoclonic SE. Non-convulsive SE (NCSE) is characterized by abnormal mental status, unresponsiveness, ocular motor abnormalities, persistent electrographic seizures, and possible response to anticonvulsants.

In embodiments, methods of treating a seizure disorder include administering (1S,3S)-3-amino-4-(difluoromethylidene)cyclopentane-1-carboxylic acid or a pharmaceutically acceptable salt thereof to a subject in need thereof wherein the subject exhibits improvement in one or more symptoms of the disorder. In embodiments, methods of treating a seizure disorder include administering (S)-3-amino-4-(difluoromethylenyl)cyclopent-1-ene-1-carboxylic acid or a pharmaceutically acceptable salt thereof, to a subject in need thereof wherein the subject exhibits improvement in one or more symptoms of the disorder.

Symptoms of a seizure disorder may include, but are not limited to, episodes involving ataxia, gait impairment, speech impairment, vocalization, impaired cognition, abnormal motor activity, clinical seizure, subclinical seizure, hypotonia, hypertonia, drooling, and mouthing behavior, aura, convulsions, repetitive movements, and unusual sensations. In embodiments, the methods and compositions provided may reduce or prevent one or more different types of seizures. Generally, a seizure can include convulsions, repetitive movements, unusual sensations, and combinations thereof. Seizures can be categorized as focal seizures (also referred to as partial seizures) and generalized seizures. Focal seizures affect only one side of the brain, while generalized seizures affect both sides of the brain. Specific types of focal seizures include simple focal seizures, complex focal seizures, and secondarily generalized seizures. Simple focal seizures can be restricted or focused on a particular lobe (e.g., temporal lobe, frontal lobe, parietal lobe, or occipital lobe). Complex focal seizures generally affect a larger part of one hemisphere than simple focal seizures, but commonly originate in the temporal lobe or the frontal lobe. When a focal seizure spreads from one side (hemisphere) to both sides of the brain, the seizure is referred to as a secondarily generalized seizure. Specific types of generalized seizures include absences (also referred to as petit mal seizures), tonic seizures, atonic seizures, myoclonic seizures, tonic clonic seizures (also referred to as grand mal seizures), and clonic seizures. Symptoms of a seizure disorder include those associated with TSC such as seizures, cognitive impairment, autism, gelastic seizures—a disorder characterized by spells of involuntary laughter with interval irritability and depressed mood. Symptoms of a seizure disorder include those associated with infantile spasms such as seizures, cognitive impairment, developmental regression, and hypsarrhythmia. Symptoms of a seizure disorder include those associated with Lennox Gastaut syndrome such as seizures, developmental delays, cognitive impairment and behavioral disturbances. Symptoms of a seizure disorder include those associated with CDKL5 disorder such as seizures, scoliosis, visual impairment, sensory issues, gastrointestinal difficulties, low or poor muscle tone, hand wringing movements or mouthing of the hands, marked developmental delay, limited or absent speech, lack of eye contact or poor eye contact, gastroesophageal reflux, constipation, small, cold feet, breathing irregularities such as hyperventilation, grinding of the teeth, episodes of laughing or crying for no reason, very limited hand skills, some autistic-like tendencies, cortical visual impairment (CVI), aka "cortical blindness", apraxia, eating/drinking challenges, sleep difficulties, characteristics such as a sideways glance, and a habit of leg crossing.

In embodiments, the terms "effective amount" or "therapeutically effective amount" as applied to a seizure disorder refer to an amount of a compound, material, composition, medicament, or other material that is effective to achieve a particular pharmacological and/or physiologic effect in connection with seizure disorder symptoms such as, but not limited to, one or more of the following: reducing or eliminating episodes involving ataxia, reducing or eliminating gait impairment, reducing or eliminating speech impairment, reducing or eliminating vocalization, reducing or eliminating impaired cognition, reducing or eliminating abnormal motor activity, reducing or eliminating clinical seizure, reducing or eliminating subclinical seizure, reducing or eliminating hypotonia, reducing or eliminating hypertonia, reducing or eliminating drooling, and mouthing behavior, reducing or eliminating aura, reducing or eliminating convulsions, reducing or eliminating repetitive movements, reducing or eliminating unusual sensations, reducing or eliminating one or more different types of seizures. reducing or eliminating convulsions, reducing or eliminating repetitive movements, reducing or eliminating unusual sensations, reducing or eliminating simple focal seizures, reducing or eliminating complex focal seizures, reducing or eliminating generalized seizures, reducing or eliminating absences (also referred to as petit mal seizures), reducing or eliminating tonic seizures, reducing or eliminating atonic seizures, reducing or eliminating myoclonic seizures, reducing or eliminating tonic clonic seizures (also referred to as grand mal seizures), reducing or eliminating clonic seizures. As examples, reducing or eliminating TSC symptoms such as seizures, cognitive impairment, autism, gelastic seizures—a disorder characterized by spells of involuntary laughter with interval irritability and depressed mood. As examples, reducing or eliminating symptoms associated with infantile spasms such as seizures, cognitive impairment, developmental regression, and hypsarrhythmia. As examples, reducing or eliminating symptoms associated with Lennox Gastaut syndrome such as seizures, developmental delays, cognitive impairment and behavioral disturbances. As examples, reducing or eliminating symptoms associated with CDKL5 disorder such as seizures, scoliosis, visual impairment, sensory issues, gastrointestinal difficulties, low or poor muscle tone, hand wringing movements or mouthing of the hands, marked developmental delay, limited or absent speech, lack of eye contact or poor eye contact, gastroesophageal reflux, constipation, small, cold feet, breathing irregularities such as hyperventilation, grinding of the teeth, episodes of laughing or crying for no reason, very limited hand skills, some autistic-like tendencies, cortical visual impairment (CVI), aka "cortical blindness", apraxia, eating/drinking challenges, sleep difficulties, characteristics such as a sideways glance, and a habit of leg crossing. In embodiments, an effective amount results in enhancing cognitive function, increasing daytime activity, improving learning (either the rate or ease of learning), improving attention, improving social behavior, and/or improving cerebrovascular function. In embodiments, effective amount refers to an amount which may be suitable to prevent a decline in any one or more of the above qualities, or, in embodiments, to improve any one or more of the above qualities. In embodiments, an effective amount may be suitable to reduce either the extent or rate of decline in a subject's cognitive skills or functioning, and/or the effective amount may be suitable to delay the onset of such decline. Such effectiveness may be achieved, for example, by administering compositions described herein to an individual or to a population. In embodiments, the reduction, or delay of such a decline, or the improvement in an individual or population can be relative to a cohort, e.g., a control subject or a cohort population that has not received the treatment, or been administered the composition or medicament.

The dosage amount can vary according to a variety of factors such as subject-dependent variables (e.g., age, immune system, health, etc.), the disease or disorder being treated, as well as the route of administration and the pharmacokinetics of the agent being administered.

Many pharmaceutical products are administered as a fixed dose, at regular intervals, to achieve therapeutic efficacy. Duration of action is typically reflected by a drug's plasma half-life. Since efficacy is often dependent on sufficient exposure within the central nervous system administration of CNS drugs with a short half-life may require frequent maintenance dosing. The plasma elimination half-life of (1S,3S)-3-amino-4-(difluoromethylidene)cyclopentane-1-carboxylic acid is between about 4 to 6 hours. $C_{max}$ increases in a dose proportional manner over a range of 5 mg-500 mg; whereas there is a greater than proportional increase in AUCs in the dose range. (S)-3-amino-4-(difluoromethylenyl)cyclopent-1-ene-1-carboxylic acid is between 9 and 10 times more potent as an inactivator of GABA-AT than (1S,3S)-3-amino-4-(difluoromethylidene)cyclopentane-1-carboxylic acid and may exhibit similar pharmacokinetics.

The structure of (1S,3S)-3-amino-4-(difluoromethylidene)cyclopentane-1-carboxylic acid may be represented as follows:

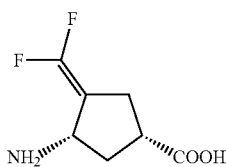 [SMILES: N[C@H]1C[C@@H](C(=O)O)CC1=C(F)F]

The structure of (S)-3-amino-4-(difluoromethylenyl)cyclopent-1-ene-1-carboxylic acid may be represented as follows:

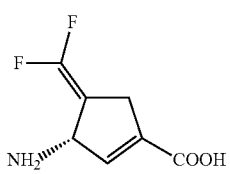

In embodiments, (1S,3S)-3-amino-4-(difluoromethylidene)cyclopentane-1-carboxylic acid may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, pantothenic, p-amino-benzoic, glutamic, benzene sulfonic or theophylline acetic acid addition salts, as well as the 8-halotheophyllines, for example 8-bromo-theophylline. In embodiments, inorganic acid addition salts, including but not limited to, hydrochloric, hydrobromic, hydroiodic, sulfuric, sulfamic, phosphoric or nitric acid addition salts may be used.

In embodiments, (S)-3-amino-4-(difluoromethylenyl)cyclopent-1-ene-1-carboxylic acid may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, pantothenic, p-amino-benzoic, glutamic, benzene sulfonic or theophylline acetic acid addition salts, as well as the 8-halotheophyllines, for example 8-bromo-theophylline. In embodiments, inorganic acid addition salts, including but not limited to, hydrochloric, hydrobromic, hydroiodic, sulfuric, sulfamic, phosphoric or nitric acid addition salts may be used.

In embodiments, methods include treating a seizure disorder by administering to a subject in need thereof about 0.1 mg to about 1500 mg of (1S,3S)-3-amino-4-difluoromethylenyl-1-cyclopentanoic acid or a pharmaceutically acceptable salt thereof, e.g., a hydrochloride salt thereof. In embodiments, methods include treating a seizure disorder by administering to a subject in need thereof about 0.5 mg to about 1000 mg of (1S,3S)-3-amino-4-difluoromethylenyl-1-cyclopentanoic acid or a pharmaceutically acceptable salt thereof, e.g., a hydrochloride salt thereof. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1500 mg/day, or 0.01 mg/kg/day to 15 mg/kg/day, for treatment of a seizure disorder. For example, the daily dosage can be, e.g., in the range of about 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 75 to 100 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for treating a seizure disorder may include (1S,3S)-3-amino-4-difluoromethylenyl-1-cyclopentanoic acid or a pharmaceutically acceptable salt thereof in an amount of, e.g., about 0.01 to 500 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject having a seizure disorder once, twice, three or four times daily, every other day, once weekly, or once a month. In embodiments, (1S,3S)-3-3-amino-4-difluoromethylenyl-1-cyclopentanoic acid or a pharmaceutically acceptable salt thereof is administered to a subject having a seizure disorder twice a day, (e.g., morning and evening), or three times a day (e.g., at breakfast, lunch, and dinner), at a dose of 1-50 mg/administration. In embodiments, (1S,3S)-3-amino-4-difluoromethylenyl-1-cyclopentanoic acid or a pharmaceutically acceptable salt thereof is administered to a subject having a seizure disorder 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 3 mg/per day, 2 mg/per day, 1 mg/per day, in one or more doses. In embodiments, an adult dose can be about 5 to 80 mg per day and can be increased to 150 mg per day. Dosages can be lower for infants and children than for adults. In embodiments, an infant or pediatric dose can be about 0.1 to 50 mg per day once or in 2, 3 or 4 divided doses. In embodiments, a pediatric dose can be 0.75 mg/kg/day to 1.5 mg/kg/day. In embodiments, the subject may be started at a low dose and the dosage is escalated over time.

In embodiments, methods of treating a seizure disorder are provided which include administering to a subject in need thereof a pharmaceutical composition including (1S, 3S)-3-amino-4-difluoromethylenyl-1-cyclopentanoic acid or a pharmaceutically acceptable salt thereof wherein the composition provides improvement in one or more symptoms of the disorder for more than 1 hour after administration to the subject. In embodiments, methods of treating a seizure disorder are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the disorder for more than 2 hours after administration to the subject. In embodiments, methods of treating a seizure disorder are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the disorder for more than 3 hours after administration to the subject. In embodiments, methods of treating a seizure disorder are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the disorder for more than 4 hours after administration to the subject. In embodiments, methods of treating a seizure disorder are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the disorder for more than 6 hours after administration to the subject. In embodiments, methods of treating a seizure disorder are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the disorder for more than 8, 10, 12, 14, 16, 18, 20, 22 or 24 hours after administration to the subject. In embodiments, improvement in at least one symptom for 12 hours after administration of the pharmaceutical composition to the subject is provided in accordance with the present disclosure. In embodiments, the pharmaceutical compositions provide improvement of next day functioning of the subject. For example, the pharmaceutical compositions may provide improvement in one or more symptoms of the disorder for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (1S,3S)-3-amino-4-difluoromethylenyl-1-cyclopentanoic acid or a pharmaceutically acceptable salt thereof is administered to a subject having a seizure disorder in combination with (S)-3-amino-4-(difluoromethylenyl)cyclopent-1-ene-1-carboxylic acid or a pharmaceutically acceptable salt thereof. In embodiments, (1S,3S)-3-amino-4-difluoromethylenyl-1-cyclopentanoic acid or a pharmaceutically acceptable salt thereof, and (S)-3-amino-4-(difluoromethylenyl)cyclopent-1-ene-1-carboxylic acid or a pharmaceutically acceptable salt thereof, may be administered to a subject having a seizure disorder in separate dosage forms or combined in one dosage form. In embodiments, (1S,3S)-3-amino-4-difluoromethylenyl-1-cyclopentanoic acid or a pharmaceutically acceptable salt thereof, and (S)-3-amino-4-(difluoromethylenyl)cyclopent-1-ene carboxylic acid or a pharmaceutically acceptable salt thereof, may be administered to a subject having a seizure disorder simultaneously or at spaced apart intervals.

In embodiments, methods include treating a seizure disorder by administering to a subject in need thereof about 0.005 mg to about 750 mg of (S)-3-amino-4-(difluoromethylenyl)cyclopent-1-ene-1-carboxylic acid or a pharmaceutically acceptable salt thereof, e.g., hydrochloride salt. In embodiments, the amount of (S)-3-amino-4-(difluoromethylenyl)cyclopent-1-ene-1-carboxylic acid or a pharmaceutically acceptable salt thereof, e.g., hydrochloride salt, can be between 0.005 and 1000 mg/day, or 0.005 mg/kg/day to 14 mg/kg/day, for treatment of a seizure disorder. For example, the daily dosage can be, e.g., in the range of about 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 6 mg, 7 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for treating a seizure disorder may include (S)-3-amino-4-(difluoromethylenyl)cyclopent-1-ene-1-carboxylic acid or a pharmaceutically acceptable salt thereof in an amount of, e.g., about 0.001 to 500 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.05 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.01 mg, 0.025 mg, 0.05 mg, 0.075 mg, 0.1 mg, 0.25 mg, 0.5 mg, 0.75 mg, 1 mg, 2 mg, 2.5 mg, 3 mg, 4 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject having a seizure disorder once, twice, three or four times daily, every other day, once weekly, or once a month. In embodiments, (S)-3-amino-4-(difluoromethylenyl)cyclopent-1-ene-1-carboxylic acid or a pharmaceutically acceptable salt thereof is administered to a subject having a seizure disorder twice a day, (e.g., morning and evening), or three times a day (e.g., at breakfast, lunch, and dinner), at a dose of 0.01-50 mg/administration. In embodiments, (S)-3-amino-4-(difluoromethylenyl)cyclopent-1-ene-1-carboxylic acid or a pharmaceutically acceptable salt thereof is administered to a subject having a seizure disorder 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 7.5 mg/per day, 5.5 mg/per day, 5 mg/per day, 4.5 mg/per day, 4 mg/per day, 3.5 mg/per day, 3 mg/per day, 2.5 mg/per day, 2 mg/per day, 1.5 mg/per day, 1 mg/per day, 0.5 mg/per day, 0.25 mg/per day, in one or more doses. In embodiments, an adult dose can be about 0.5 to 50 mg per day and can be increased to 75 mg per day. Dosages can be lower for infants and children than for adults. In embodiments, an infant or pediatric dose can be from about 0.01 to 10 mg per day once or in 2, 3 or 4 divided doses. In embodiments, a pediatric dose can be 0.075 mg/kg/day to 1.0 mg/kg/day. In embodiments, the subject may be started at a low dose and the dosage is escalated over time.

In embodiments, methods of treating a seizure disorder are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of the disorder for more than 1 hour after administration to the subject. In embodiments, methods of treating a seizure disorder are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of the disorder for more than 2 hours after administration to the subject. In embodiments, methods of treating a seizure disorder are provided which include administering to a subject in need thereof a pharmaceutical composition including (including (S)-3-amino (difluoromethylenyl)cyclopent-1-ene-1-carboxylic acid or a pharmaceutically acceptable salt thereof wherein the composition provides improvement in one or more symptoms of the disorder for more than 3 hours after administration to the subject. In embodiments, methods of treating a seizure disorder are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of the disorder for more than 4 hours after administration to the subject. In embodiments, methods of treating a seizure disorder are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of the disorder for more than 6 hours after administration to the subject. In embodiments, methods of treating a seizure disorder are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of the disorder for more than 8, 10, 12, 14, 16, 18, 20, 22 or 24 hours after administration to the subject. In embodiments, improvement in at least one symptom for 12 hours after administration of the pharmaceutical composition to the subject is provided in accordance with the present disclosure. In embodiments, the pharmaceutical compositions provide improvement of next day functioning of the subject. For example, the pharmaceutical compositions may provide improvement in one or more symptoms of the disorder for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (S)-3-amino-4-(difluoromethylenyl)cyclopent-1-ene-1-carboxylic acid or a pharmaceutically acceptable salt thereof or a pharmaceutically acceptable salt thereof may be administered to a subject having a seizure disorder in combination with (1S,3S)-3-amino-4-difluoromethylenyl-1-cyclopentanoic acid or a pharmaceutically acceptable salt thereof. In embodiments, (S)-3-amino-4-(difluoromethylenyl)cyclopent-1-ene-1-carboxylic acid or a pharmaceutically acceptable salt thereof, and (1S,3S)-3-amino-4-difluoromethylenyl cyclopentanoic acid or a pharmaceutically acceptable salt thereof, may be administered to a subject having a seizure disorder in separate dosage forms or combined in one dosage form. In embodiments, (S)-3-amino-4-(difluoromethylenyl)cyclopent-1-ene-1-carboxylic acid or a pharmaceutically acceptable salt thereof, and (1S,3S)-3-amino-4-difluoromethylenyl-1-cyclopentanoic acid or a pharmaceutically acceptable salt thereof, may be administered to a subject having a seizure disorder simultaneously or at spaced apart intervals.

In embodiments, provided herein are methods of treating a seizure disorder including administering to a subject in need thereof a pharmaceutical composition including (1S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt of any of the preceding, after a warning sign of an impending seizure is detected to reduce or prevent seizure activity. In embodiments, provided herein are methods of treating a seizure disorder including administering to a subject in need thereof a pharmaceutical composition including (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt of any of the preceding, after a warning sign of an impending seizure is detected to reduce or prevent seizure activity. In embodiments, a continuing regimen of administration of active agents herein (one or both of (S)-3-amino-4-(difluoromethylenyl)cyclopent-1-ene-1-carboxylic acid, or (1S,3S)-3-amino-4-(difluoromethylidene)cyclopentane-1-carboxylic acid, or a pharmaceutically acceptable salt of any of the preceding) is effective to reduce or prevent occurrence of seizure activity.

In embodiments, the methods described herein are effective to reduce, delay, or prevent one or more other clinical symptoms of a seizure disorder. For example, the effect of a composition including: 1. (1S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid, or a pharmaceutically acceptable salt of any of the preceding, or 2. (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid, or a pharmaceutically acceptable salt of any of the preceding, on a particular symptom, pharmacologic, or physiologic indicator can be compared to an untreated subject, or the condition of the subject prior to treatment. In embodiments, the symptom, pharmacologic, and/or physiologic indicator is measured in a subject prior to treatment, and again one or more times after treatment is initiated. In embodiments, the control is a reference level, or average determined based on measuring the symptom, pharmacologic, or physiologic indicator in one or more subjects that do not have the disease or condition to be treated (e.g., healthy subjects). In embodiments, the effect of the treatment is compared to a conventional treatment that is known the art.

Effective treatment of a seizure disorder (e.g., acute repetitive seizure, status epilepticus) herein may be established by showing reduction in the frequency or severity of symptoms (e.g., more than, e.g., 10%, 20%, 30% 40%, 50% or more) after a period of time compared with baseline. For example, after a baseline period of 1 month, the subjects may be randomly allocated: 1. (1S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt of any of the preceding, or 2. (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt of any of the preceding, or placebo as add-on therapy to standard therapies, during a double-blind period of 2 months.

Primary outcome measurements may include the percentage of responders on: 1. (1S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt of any of the preceding, or 2. (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt of any of the preceding, and on placebo, defined as having experienced at least a 10% to 50% or more reduction of symptoms during the second month of the double-blind period compared with baseline.

In embodiments, administration of (1S,3S)-3-amino-4-(difluoromethylidene)cyclopentane-1-carboxylic, or (S)-3-amino-4-(difluoromethylenyl)cyclopent-1-ene-1-carboxylic acid, or a pharmaceutically acceptable salt of any of the preceding, either alone or in combination, may be used to prevent epilepsy when administration occurs before seizures manifest themselves in a subject. Detecting abnormal EEG signature in a subject provides a modality for predicting developing epilepsy in the subject. For example, patients diagnosed with TSC are at high risk of developing epilepsy, including infantile spasms and neurological deficits such as cognitive impairment. An abnormal EEG signature such as multifocal spikes in infants diagnosed with TSC serves to identify candidates for antiepileptogenic therapy with (1S,3S)-3-amino-4-(difluoromethylidene)cyclopentane-1-carboxylic acid, or (S)-3-amino-4-(difluoromethylenyl)cyclopent-1-ene-1-carboxylic acid, or a pharmaceutically acceptable salt of any of the preceding, either alone or in any combination of one or more of the preceding, which is implemented before seizures occur or shortly thereafter. In other words, antiepileptogenic treatment at an early stage of epileptogenesis is instituted. In this manner, the neurological outcome of the subject is improved. Improved neurological outcome refers to a decrease in or elimination of one or more symptoms associated with a seizure disorder. Accordingly, (1S,3S)-3-amino-4-(difluoromethylidene)cyclopentane-1-carboxylic acid, or (S)-3-amino-4-(difluoromethylenyl)cyclopent-1-ene-1-carboxylic acid, or a pharmaceutically acceptable salt of any of the preceding, either alone or in combination, are used to treat abnormal EEG signature.

Methods of treating Prader-Willi syndrome are provided herein and, in embodiments, include administering to a subject in need thereof an effective amount of (1S,3S)-3-amino-4-(difluoromethylidene)cyclopentane-1-carboxylic acid or a pharmaceutically acceptable salt thereof. In embodiments, methods of treating Prader-Willi syndrome include administering (1S,3S)-3-amino-4-(difluoromethylidene)cyclopentane-1-carboxylic acid or a pharmaceutically acceptable salt thereof to a subject in need thereof to provide improvement in one or more symptoms of the syndrome. In embodiments, methods of treating Prader-Willi syndrome include administering (1S,3S)-3-amino-4-(difluoromethylidene)cyclopentane-1-carboxylic acid or a pharmaceutically acceptable salt thereof to a subject in need thereof to provide improvement in next day functioning of the subject. In embodiments, methods of treating Prader-Willi syndrome include administering to a subject in need thereof an effective amount of (S)-3-amino-4-(difluoromethylenyl)cyclopent-1-ene-1-carboxylic acid or a pharmaceutically acceptable salt thereof. In embodiments, methods of treating Prader-Willi Syndrome include administering (S)-3-amino-4-(difluoromethylenyl)cyclopent-1-ene-1-carboxylic acid or a pharmaceutically acceptable salt thereof to a subject in need thereof to provide improvement in one or more symptoms of the syndrome. In embodiments, methods of treating Prader-Willi Syndrome include administering (S)-3-amino-4-(difluoromethylenyl)cyclopent-1-ene-1-carboxylic acid or a pharmaceutically acceptable salt thereof to a subject in need thereof to provide improvement in next day functioning of the subject. In embodiments, methods of treating Prader-Willi syndrome include administering (1S,3S)-3-amino-4-(difluoromethylidene)cyclopentane-1-carboxylic acid or a pharmaceutically acceptable salt thereof, in combination with (S)-3-amino-4-(difluoromethylenyl)cyclopent-1-ene-1-carboxylic acid or a pharmaceutically acceptable salt thereof, to a subject in need thereof.

Symptoms of Prader-Willi syndrome include hypotonia, difficulty in sucking, difficulty in feeding, poor muscle tone, growth hormone deficiency, low levels of sex hormones, a constant feeling of hunger, excessive appetite (hyperphagia), weight gain, obesity, short stature, poor motor skills, underdeveloped sex organs, intellectual disability, learning disability, delayed speech development, delayed language development, infertility, cognitive rigidity, cognitive impairment, emotional lability, obsessive-compulsive behavior, autistic symptomology, excessive daytime sleepiness, scoliosis, osteopenia/osteoporosis, decreased gastrointestinal motility, sleep disturbances, and/or reduced pain sensitivity. In addition, in approximately 10% of individuals with PWS, more severe psychiatric illness can result including psychotic episodes, depression and bipolar disorder with psychosis.

Criteria regarding learning disorders which may be manifest in seizure disorders or Prader-Willi syndrome are provided in the DSM-5 that considers specific learning disabilities to be a type of neurodevelopmental disorder that impedes the ability to learn or use specific academic skills (e.g., reading, writing, or arithmetic), which are the foundation for other learning.

Cognitive impairment (aka impairment of cognition), whether applied to seizure disorders or Prader-Willi syndrome, may be measured against normal cognitive function, which refers to the normal physiologic activity of the brain, including, but not limited to, one or more of the following: mental stability, memory/recall abilities, problem solving abilities, reasoning abilities, thinking abilities, judging abilities, ability to discriminate or make choices, capacity for learning, ease of learning, perception, intuition, attention, and awareness, as measured by any criteria suitable in the art.

Cognitive impairment also includes deficits in mental activities that are mild or that otherwise do not significantly interfere with daily life. Mild cognitive impairment (MCI) is an example of such a condition. A subject with mild cognitive impairment may display symptoms of dementia (e.g., difficulties with language or memory) but the severity of these symptoms is such that a diagnosis of dementia may not be appropriate.

One skilled in the art will appreciate that there are numerous human and animal models that may be used to evaluate and compare the relative safety and efficacy of compounds described herein for the treatment of cognitive impairment associated with seizure disorders or Prader-Willi syndrome. In humans, cognitive function may be measured, for example and without limitation, by the clinical global impression of change scale (CGI); the Mini Mental State Exam (MMSE) (aka the Folstein Test); the Neuropsychiatric Inventory (NPI); the Clinical Dementia Rating Scale (CDR); the Cambridge Neuropsychological Test Automated Battery (CANTAB), the Sandoz Clinical Assessment-Geriatric (SCAG) scale, the Benton Visual Retention Test (BVRT), Montreal Cognitive Assessment (MoCA) or Digit Symbol Substitution Test (DSST).

In animal model systems, cognitive function may be measured in various conventional ways known in the art, including using a Morris Water Navigation Task, Barnes maze, radial arm maze task, T maze and the like. Other tests known in the art may also be used to assess cognitive function, such as novel object recognition and odor recognition tasks.

Cognitive function may also be measured using imaging techniques such as Positron Emission Tomography (PET), functional magnetic resonance imaging (fMRI), Single Photon Emission Computed Tomography (SPECT), or any other imaging technique that allows one to measure brain function. In animals, cognitive function may also be measured with electrophysiological techniques.

Accordingly, an effective amount of (1S,3S)-3-amino-4-(difluoromethylidene)cyclopentane-1-carboxylic acid or a pharmaceutically acceptable salt thereof is used to treat a subject having Prader-Willi syndrome. An effective amount of (S)-3-amino-4-(difluoromethylenyl)cyclopent-1-ene-1-carboxylic acid or a pharmaceutically acceptable salt thereof is used to treat a subject having Prader-Willi syndrome. The subject may be an animal, e.g., mammal, e.g., human, etc. As used herein, whether applied to seizure disorders or Prader-Willi syndrome, the terms "treat", "treatment" or "treating" encompass any manner in which the symptoms or pathology of a condition, disorder or disease associated with seizure disorders or Prader-Willi syndrome are ameliorated or otherwise beneficially altered. In embodiments, "treat", "treatment" or "treating" can refer to inhibiting a disease or condition, e.g., arresting or reducing its development or at least one clinical or subclinical symptom thereof. In embodiments, "treat", "treatment" or "treating" can refer to relieving the disease or condition, e.g., causing regression of the disease or condition or at least one of its clinical or subclinical symptoms. In embodiments, "treating cognitive impairment" means ameliorating, beneficially altering and/or providing relief from one or more of the symptoms of cognitive impairment. The benefit to a subject being treated may be statistically significant, mathematically significant, or at least perceptible to the subject and/or the physician.

In embodiments, the terms "effective amount" or "therapeutically effective amount" as applied to PWS refer to an amount of a compound, material, composition, medicament, or other material that is effective to achieve a particular pharmacological and/or physiologic effect in connection with PWS symptoms such as, but not limited to, one or more of the following: reducing or eliminating difficulty in sucking, reducing or eliminating difficulty in feeding, reducing or eliminating poor muscle tone, reducing or eliminating growth hormone deficiency, increasing levels of sex hormones, reducing or eliminating a constant feeling of hunger, reducing or eliminating excessive appetite (hyperphagia), reducing or eliminating weight gain, reducing or eliminating obesity, reducing or eliminating short stature, increasing motor skills, reducing or eliminating underdeveloped sex organs, reducing or eliminating intellectual disability, reducing or eliminating learning disability, reducing or eliminating delayed speech development, reducing or eliminating delayed language development, reducing or eliminating infertility, reducing or eliminating cognitive rigidity, reducing or eliminating cognitive impairment, reducing or eliminating emotional lability, reducing or eliminating obsessive-compulsive behavior, reducing or eliminating autistic symptomology, reducing or eliminating psychotic episodes, reducing or eliminating bipolar disorder with psychosis, reducing or eliminating excessive daytime sleepiness, reducing or eliminating scoliosis, reducing or eliminating osteopenia/osteoporosis, reducing or eliminating decreased gastrointestinal motility, reducing or eliminating sleep disturbances, and/or reducing or eliminating reduced pain sensitivity, enhancing cognitive function, increasing daytime activity, improving learning (either the rate or ease of learning), improving attention, improving social behavior, and/or improving cerebrovascular function. In embodiments, effective amount refers to an amount which may be suitable to prevent a decline in any one or more of the above qualities, or, in embodiments, to improve any one or more of the above qualities, for example, constant feeling of hunger, excessive appetite (hyperphagia), weight gain, obesity, cognitive function or performance, learning rate or ability, problem solving ability, attention span and ability to focus on a task or problem, social behavior, and the like. In embodiments, an effective amount may be suitable to reduce either the extent or rate of decline in a subject's appetite dysregulation, weight loss, cognitive skills or functioning, and/or the effective amount may be suitable to delay the onset of such decline. In embodiments, an effective amount increases hypothalamic BDNF expression. Such effectiveness may be achieved, for example, by administering compositions described herein to an individual or to a population. In embodiments, the reduction, or delay of such a decline, or the improvement in an individual or population can be relative to a cohort, e.g., a control subject or a cohort population that has not received the treatment, or been administered the composition or medicament.

The dosage amount can vary according to a variety of factors such as subject-dependent variables (e.g., age, immune system, health, etc.), the disease or disorder being treated, as well as the route of administration and the pharmacokinetics of the agent being administered.

In embodiments, methods include treating PWS by administering to a subject in need thereof about 0.1 mg to about 1500 mg of (1S,3S)-3-amino-4-difluoromethylenyl-1-cyclopentanoic acid or a pharmaceutically acceptable salt thereof, e.g., a hydrochloride salt thereof. In embodiments, methods include treating PWS by administering to a subject in need thereof about 0.5 mg to about 1000 mg of (1S,3S)-3-amino-4-difluoromethylenyl-1-cyclopentanoic acid or a pharmaceutically acceptable salt thereof, e.g., a hydrochloride salt thereof. In embodiments, the amount of (1S,3S)-3-amino difluoromethylenyl-1-cyclopentanoic acid or a pharmaceutically acceptable salt thereof, e.g., a hydrochloride salt thereof, can be between 0.1 and 1500 mg/day, or 0.01 mg/kg/day to 15 mg/kg/day, for treatment of PWS. In embodiments, the amount of (1S,3S)-3-amino-4-difluoromethylenyl cyclopentanoic acid or a pharmaceutically acceptable salt thereof, e.g., a hydrochloride salt thereof, can be between 0.1 and 1000 mg/day for treatment of PWS. For example, the daily dosage can be, e.g., in the range of about 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions may include (1S,3S)-3-amino-4-difluoromethylenyl-1-cyclopentanoic acid or a pharmaceutically acceptable salt thereof in an amount of, e.g., about 0.01 to 500 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages for treating PWS may be administered to a subject once, twice, three or four times daily, every other day, once weekly, or once a month. In embodiments, (1S, 3S)-3-amino-4-difluoromethylenyl-1-cyclopentanoic acid or a pharmaceutically acceptable salt thereof is administered to a subject twice a day, (e.g., morning and evening), or three times a day (e.g., at breakfast, lunch, and dinner), at a dose of 1-50 mg/administration. In embodiments, (1S,3S)-3-amino-4-difluoromethylenyl-1-cyclopentanoic acid or a pharmaceutically acceptable salt thereof is administered to a subject 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 2 mg/per day, 1 mg/per day, in one or more doses. In embodiments, an adult dose for treating PWS can be about 5 to 80 mg per day and can be increased to 150 mg per day. Dosages can be lower for infants and children than for adults. In embodiments, an infant or pediatric dose for treating PWS can be about 0.1 to 50 mg per day once or in 2, 3 or 4 divided doses. In embodiments, a pediatric dose for treating PWS can be 0.75 mg/kg/day to 1.5 mg/kg/day. In embodiments, the subject may be started at a low dose and the dosage is escalated over time.

In embodiments, (1S,3S)-3-amino-4-difluoromethylenyl-1-cyclopentanoic acid or a pharmaceutically acceptable salt thereof is administered via a pharmaceutical composition for treatment of either seizure disorders or PWS. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating PWS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the syndrome for more than 1 hour after administration to the subject. In embodiments, methods of treating PWS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the syndrome for more than 2 hours after administration to the subject. In embodiments, methods of treating PWS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the syndrome for more than 3 hours after administration to the subject. In embodiments, methods of treating PWS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the syndrome for more than 4 hours after administration to the subject. In embodiments, methods of treating PWS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the syndrome for more than 6 hours after administration to the subject. In embodiments, methods of treating PWS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of the syndrome for more than 8, 10, 12, 14, 16, 18, 20, 22 or 24 hours after administration to the subject. In embodiments, the pharmaceutical compositions provide improvement of next day functioning of the subject. For example, the pharmaceutical compositions may provide improvement in one or more symptoms of the syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (1S,3S)-3-amino-4-difluoromethylenyl-1-cyclopentanoic acid or a pharmaceutically acceptable salt thereof is administered to a subject having PWS in combination with (S)-3-amino-4-(difluoromethylenyl)cyclopent-1-ene-1-carboxylic acid or a pharmaceutically acceptable salt thereof. In embodiments, (1S,3S)-3-amino-4-difluoromethylenyl-1-cyclopentanoic acid or a pharmaceutically acceptable salt thereof, and (S)-3-amino-4-(difluoromethylenyl)cyclopent-1-ene-1-carboxylic acid or a pharmaceutically acceptable salt thereof, may be administered to a subject having PWS in separate dosage forms or combined in one dosage form. In embodiments, (1S,3S)-3-amino-4-difluoromethylenyl-1-cyclopentanoic acid or a pharmaceutically acceptable salt thereof, and (S)-3-amino-4-(difluoromethylenyl)cyclopent-1-ene-1-carboxylic acid or a pharmaceutically acceptable salt thereof, may be administered to a subject having PWS simultaneously or at spaced apart intervals.

In embodiments, methods include treating PWS by administering to a subject in need thereof about 0.005 mg to about 750 mg of (S)-3-amino-4-(difluoromethylenyl)cyclopent-1-ene-1-carboxylic acid or a pharmaceutically acceptable salt thereof, e.g., hydrochloride salt. In embodiments, the amount of (S)-3-amino-4-(difluoromethylenyl)cyclopent-1-ene-1-carboxylic acid or a pharmaceutically acceptable salt thereof, e.g., hydrochloride salt, can be between 0.005 and 1000 mg/day, or 0.005 mg/kg/day to 14 mg/kg/day, for treatment of PWS. For example, the daily dosage can be, e.g., in the range of about 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 6 mg, 7 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions may include (S)-3-amino-4-(difluoromethylenyl)cyclopent-1-ene-1-carboxylic acid or a pharmaceutically acceptable salt thereof in an amount of, e.g., about 0.001 to 500 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.05 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.01 mg, 0.025 mg, 0.05 mg, 0.075 mg, 0.1 mg, 0.25 mg, 0.5 mg, 0.75 mg, 1 mg, 2 mg, 2.5 mg, 3 mg, 4 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject once, twice, three or four times daily, every other day, once weekly, or once a month. In embodiments, (S)-3-amino-4-(difluoromethylenyl) cyclopent-1-ene-1-carboxylic acid or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, (S)-3-amino-4-(difluoromethylenyl)cyclopent-1-ene-1-carboxylic acid or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 7.5 mg/per day, 5.5 mg/per day, 5 mg/per day, 4.5 mg/per day, 4 mg/per day, 3.5 mg/per day, 3 mg/per day, 2.5 mg/per day, 2 mg/per day, 1.5 mg/per day, 1 mg/per day, 0.5 mg/per day, 0.25 mg/per day, in one or more doses. In embodiments, an adult dose for treating PWS can be about 0.5 to 50 mg per day and can be increased to 75 mg per day. Dosages can be lower for infants and children than for adults. In embodiments, an infant or pediatric dose for treating PWS can be from about 0.01 to 10 mg per day once or in 2, 3 or 4 divided doses. In embodiments, a pediatric dose for treating PWS can be 0.075 mg/kg/day to 50 mg/kg/day. In embodiments, the subject may be started at a low dose and the dosage is escalated over time.

In embodiments, for treatment of seizure disorders or PWS, (S)-3-amino (difluoromethylenyl)cyclopent-1-ene-1-carboxylic acid or a pharmaceutically acceptable salt thereof is administered via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating PWS are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of the syndrome for more than 1 hour after administration to the subject. In embodiments, methods of treating PWS are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of the syndrome for more than 2 hours after administration to the subject. In embodiments, methods of treating PWS are provided which include administering to a subject in need thereof a pharmaceutical composition including (including (S)-3-amino-4-(difluoromethylenyl)cyclopent-1-ene-1-carboxylic acid or a pharmaceutically acceptable salt thereof wherein the composition provides improvement in one or more symptoms of the syndrome for more than 3 hours after administration to the subject. In embodiments, methods of treating PWS are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of the syndrome for more than 4 hours after administration to the subject. In embodiments, methods of treating PWS are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of the syndrome for more than 6 hours after administration to the subject. In embodiments, methods of treating PWS are provided which include administering to a subject in need thereof a pharmaceutical composition including (S)-3-amino (difluoromethylenyl)cyclopent-1-ene-1-carboxylic acid or a pharmaceutically acceptable salt thereof wherein the composition provides improvement in one or more symptoms of the syndrome for more than 8, 10, 12, 14, 16, 18, 20, 22 or 24 hours after administration to the subject. In embodiments, the pharmaceutical compositions provide improvement of next day functioning of the subject. For example, the pharmaceutical compositions may provide improvement in one or more symptoms of the syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (S)-3-amino-4-(difluoromethylenyl)cyclopent-1-ene-1-carboxylic acid or a pharmaceutically acceptable salt thereof or a pharmaceutically acceptable salt thereof is administered to a subject having PWS in combination with (1S,3S)-3-amino-4-difluoromethylenyl-1-cyclopentanoic acid or a pharmaceutically acceptable salt thereof. In embodiments, (S)-3-amino-4-(difluoromethylenyl)cyclopent-1-ene-1-carboxylic acid or a pharmaceutically acceptable salt thereof, and (1S,3S)-3-amino-4-difluoromethylenyl-1-cyclopentanoic acid or a pharmaceutically acceptable salt thereof, may be administered to a subject having PWS in separate dosage forms or combined in one dosage form. In embodiments, (S)-3-amino-4-(difluoromethylenyl)cyclopent-1-ene-1-carboxylic acid or a pharmaceutically acceptable salt thereof, and (1S,3S)-3-amino-4-difluoromethylenyl-1-cyclopentanoic acid or a pharmaceutically acceptable salt thereof, may be administered to a subject having PWS simultaneously or at spaced apart intervals.

In embodiments, provided herein are methods of treating PWS or a seizure disorder including administering to a subject in need thereof (1S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt of any of the preceding, which provides an in vivo plasma profile, wherein the in vivo plasma profile of the subject 10 hours after administration of (1S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt of any of the preceding, is reduced by more than 50% and the method provides improvement in the subject for more than 10, 12, 14, 16, 18, 20, 22 or 24 hours after administration. In embodiments, provided herein are methods of treating PWS or a seizure disorder including administering to a subject in need thereof (S)-3-amino (difluoromethylenyl)cyclopent-1-ene-1-carboxylic acid or a pharmaceutically acceptable salt thereof, either alone or in combination with (1S,3S)-3-amino-4-(difluoromethylidene)cyclopentane carboxylic acid or a pharmaceutically acceptable salt of any of the preceding, which provides an in vivo plasma profile, wherein the in vivo plasma profile of the subject 10 hours after administration of (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt of any of the preceding, is reduced by more than 50% and the method provides improvement in the subject for more than 10, 12, 14, 16, 18, 20, 22 or 24 hours after administration.

In embodiments, provided herein are methods of treating PWS or a seizure disorder including administering to a subject in need thereof (1S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt of any of the preceding, which provides an in vivo plasma profile, wherein the in vivo plasma profile of the subject 10 hours after administration of (1S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt of any of the preceding, is reduced by more than 55% and the method provides improvement in the subject for more than 10, 12, 14, 16, 18, 20, 22 or 24 hours after administration. In embodiments, provided herein are methods of treating PWS or a seizure disorder including administering to a subject in need thereof (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt of any of the preceding, which provides an in vivo plasma profile, wherein the in vivo plasma profile of the subject 10 hours after administration of (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt of thereof, is reduced by more than 55% and the method provides improvement in the subject for more than 10, 12, 14, 16, 18, 20, 22 or 24 hours after administration.

In embodiments, provided herein are methods of treating PWS or a seizure disorder including administering to a subject in need thereof (1S,3S)-3-amino-4-(difluoromethylidene)cyclopentane carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt thereof, which provides an in vivo plasma profile, wherein the in vivo plasma profile of the subject 10 hours after administration of (1S,3S)-3-amino (difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt thereof, is reduced by more than 60% and the method provides improvement in the subject for more than 10, 12, 14, 16, 18, 20, 22 or 24 hours after administration. In embodiments, provided herein are methods of treating PWS or a seizure disorder including administering to a subject in need thereof (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic or a pharmaceutically acceptable salt thereof, which provides an in vivo plasma profile, wherein the in vivo plasma profile of the subject 10 hours after administration of (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt thereof, is reduced by more than 60% and the method provides improvement in the subject for more than 10, 12, 14, 16, 18, 20, 22 or 24 hours after administration. in the subject for more than 10, 12, 14, 16, 18, 20, 22 or 24 hours after administration.

In embodiments, provided herein are methods of treating PWS or a seizure disorder including administering to a subject in need thereof (1S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt thereof, which provides an in vivo plasma profile, wherein the in vivo plasma profile of the subject 10 hours after administration of (1S,3S)-3-amino-4-(difluoromethylidene)cyclopentane-1-carboxylic acid or a pharmaceutically acceptable salt thereof, either alone or in combination with (S)-3-amino-4-(difluoromethylenyl)cyclopent-1-ene-1-carboxylic acid or a pharmaceutically acceptable salt thereof, is reduced by more than 65% and the method provides improvement in the subject for more than 10, 12, 14, 16, 18, 20, 22 or 24 hours after administration. In embodiments, provided herein are methods of treating PWS or a seizure disorder including administering to a subject in need thereof (S)-3-amino-4-(difluoromethylenyl)cyclopent-1-ene-1-carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt thereof, which provides an in vivo plasma profile, wherein the in vivo plasma profile of the subject 10 hours after administration of (S)-3-amino-4-(difluoromethylenyl)cyclopent-1-ene carboxylic acid or a pharmaceutically acceptable salt thereof, either alone or in combination with (1S,3S)-3-amino-4-(difluoromethylidene)cyclopentane-1-carboxylic acid or a pharmaceutically acceptable salt thereof, is reduced by more than 65% and the method provides improvement in the subject for more than 10, 12, 14, 16, 18, 20, 22 or 24 hours after administration.

In embodiments, provided herein are methods of treating PWS or a seizure disorder wherein the amount of active substance, e.g., (1S,3S)-3-amino-4-(difluoromethylidene)cyclopentane-1-carboxylic acid, (S)-3-amino-4-(difluoromethylenyl)cyclopent-1-ene-1-carboxylic acid (KT-II-115), or a pharmaceutically acceptable salt of any of the preceding, individually or in combination, within the subject about 4 hours after administration of the pharmaceutical composition is less than about 75% of the administered dose. In embodiments, provided herein are methods wherein the amount of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, individually or in any combination, within the subject about, e.g., 6 hours, 8 hours, 10 hours, 12 hours, 15 hours, or 20 hours after administration of the pharmaceutical composition is less than about 75%.

In embodiments, provided herein are methods of treating PWS or a seizure disorder wherein the amount of active substance, e.g., (1S,3S)-3-amino-4-(difluoromethylidene) cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, individually or in any combination, within the subject about 4 hours after administration of the pharmaceutical composition is less than about 80% of the administered dose. In embodiments, provided herein are methods wherein the amount of active substance, e.g., (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, individually or in any combination, within the subject about, e.g., 6 hours, 8 hours, 10 hours, 12 hours, 15 hours, or 20 hours after administration of the pharmaceutical composition is less than about 80% of the administered dose.

In embodiments, provided herein are methods of treating PWS or a seizure disorder wherein the amount of active substance, e.g., (1S,3S)-3-amino-4-(difluoromethylidene) cyclopentane carboxylic acid, or (S)-3-amino-4-(difluoromethylenyl)cyclopent-1-ene-1-carboxylic acid (KT-II-115), or a pharmaceutically acceptable salt of any of the preceding, individually or in any combination, within the subject about 4 hours after administration of the pharmaceutical composition is between about 65% to about 85% of the administered dose. In embodiments, the amount of active substance, e.g., (1S,3S)-3-amino-4-(difluoromethylidene)cyclopentane-1-carboxylic acid, or (S) amino-4-(difluoromethylenyl) cyclopent-1-ene-1-carboxylic acid (KT-II-115), or a pharmaceutically acceptable salt of any of the preceding, individually or in any combination, within the subject after about, e.g., 6 hours, 8 hours, 10 hours, 12 hours, 15 hours, or 20 hours after administration of the pharmaceutical composition is between about 65% to about 85% of the administered dose.

In embodiments, the pharmaceutical compositions described herein may be administered once daily, twice daily, three times daily, four times daily, or every other day. In embodiments, the pharmaceutical compositions described herein may be administered by continuous infusion. In embodiments, a pharmaceutical composition described herein is provided to the subject in the morning. In embodiments, a pharmaceutical composition described herein is provided to the subject in the evening. In embodiments, a pharmaceutical composition described herein is provided to the subject once in the evening and once in the morning. In embodiments, a pharmaceutical composition described herein is provided to the subject once in the morning, once in the afternoon and once in the evening.

In embodiments, as mentioned previously, pharmaceutical compositions herein may be provided with conventional release or modified release profiles. Pharmaceutical compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions. Those with skill in the art are familiar with such pharmaceutical carriers and methods of compounding pharmaceutical compositions using such carriers.

In embodiments, pharmaceutical compositions herein are modified release dosage forms which provide modified release profiles. Modified release profiles may exhibit immediate release, delayed release, or extended release profiles. Conventional (or unmodified) release oral dosage forms such as tablets, capsules, suppositories, syrups, solutions and suspensions typically release medications into the mouth, stomach or intestines as the tablet, capsule shell or suppository dissolves, or, in the case of syrups, solutions and suspensions, when they are swallowed. The pattern of drug release from modified release (MR) dosage forms is deliberately changed from that of a conventional dosage form to achieve a desired therapeutic objective and/or better patient compliance. Types of MR drug products include orally disintegrating dosage forms (ODDFs) which provide immediate release, extended release dosage forms, delayed release dosage forms (e.g., enteric coated), and pulsatile release dosage forms.

An ODDF is a solid dosage form containing a medicinal substance or active ingredient which disintegrates rapidly, usually within a matter of seconds when placed upon the tongue. The disintegration time for ODDFs generally range from one or two seconds to about a minute. ODDFs are designed to disintegrate or dissolve rapidly on contact with saliva. This mode of administration can be beneficial to people who may have problems swallowing tablets whether it be from physical infirmity or psychiatric in nature. Subjects with PWS or seizure disorders may exhibit such behavior. ODDF's can provide rapid delivery of medication to the blood stream through mucosa resulting in a rapid onset of action. Examples of ODDFs include orally disintegrating tablets, capsules and rapidly dissolving films and wafers.

Extended release dosage forms (ERDFs) have extended release profiles and are those that allow a reduction in dosing frequency as compared to that presented by a conventional dosage form, e.g., a solution or unmodified release dosage form. ERDFs provide a sustained duration of action of a drug. Suitable formulations which provide extended release profiles are well-known in the art. For example, coated slow release beads or granules ("beads" and "granules" are used interchangeably herein) in which one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, is applied to beads, e.g., confectioners nonpareil beads, and then coated with conventional release retarding materials such as waxes, enteric coatings and the like. In embodiments, beads can be formed in which one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, is mixed with a material to provide a mass from which the drug leaches out. In embodiments, the beads may be engineered to provide different rates of release by varying characteristics of the coating or mass, e.g., thickness, porosity, using different materials, etc. Beads having different rates of release may be combined into a single dosage form to provide variable or continuous release. The beads can be contained in capsules or compressed into tablets.

In embodiments, modified dosage forms herein incorporate delayed release dosage forms having delayed release profiles. Delayed release dosage forms can include delayed release tablets or delayed release capsules. A delayed release tablet is a solid dosage form which releases a drug (or drugs) such as one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, at a time other than promptly after administration. A delayed release capsule is a solid dosage form in which the drug is enclosed within either a hard or soft soluble container made from a suitable form of gelatin, and which releases a drug (or drugs) at a time other than promptly after administration. For example, enteric-coated tablets, capsules, particles and beads are well-known examples of delayed release dosage forms. Enteric coated tablets, capsules and particles and beads pass through the stomach and release the drug in the intestine. In embodiments, a delayed release tablet is a solid dosage form containing a conglomerate of medicinal particles that releases a drug (or drugs) at a time other than promptly after administration. In embodiments, the conglomerate of medicinal particles are covered with a coating which delays release of the drug. In embodiments, a delayed release capsule is a solid dosage form containing a conglomerate of medicinal particles that releases a drug (or drugs) at a time other than promptly after administration. In embodiments, the conglomerate of medicinal particles are covered with a coating which delays release of the drug.

Delayed release dosage forms are known to those skilled in the art. For example, coated delayed release beads or granules in which one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, is applied to beads, e.g., confectioners nonpareil beads, and then coated with conventional release delaying materials such as waxes, enteric coatings and the like. In embodiments, beads can be formed in which one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, is mixed with a material to provide a mass from which the drug leaches out. In embodiments, the beads may be engineered to provide different rates of release by varying characteristics of the coating or mass, e.g., thickness, porosity, using different materials, etc. In embodiments, enteric coated granules of one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, can be contained in an enterically coated capsule or tablet which releases the granules in the small intestine. In embodiments, the granules have a coating which remains intact until the coated granules reach at least the ileum and thereafter provide a delayed release of the drug in the colon. Suitable enteric coating materials are well known in the art, e.g., Eudragit® coatings such methacrylic acid and methyl methacrylate polymers and others. The granules can be contained in capsules or compressed into tablets.

In embodiments, one or both of (1S,3S)-3-amino-4-(difluoromethylidene)cyclopentane carboxylic acid, or (S)-3-amino-4-(difluoromethylenyl)cyclopent-1-ene-1-carboxylic acid (KT-II-115), or a pharmaceutically acceptable salt of any of the preceding, is incorporated into porous inert carriers that provide delayed release profiles. In embodiments, the porous inert carriers incorporate channels or passages from which the drug diffuses into surrounding fluids. In embodiments, one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, is incorporated into an ion-exchange resin to provide a delayed release profile. Delayed action may result from a predetermined rate of release of the drug from the resin when the drug-resin complex contacts gastrointestinal fluids and the ionic constituents dissolved therein. In embodiments, membranes are utilized to control rate of release from drug containing reservoirs. In embodiments, liquid preparations may also be utilized to provide a delayed release profile. For example, a liquid preparation consisting of solid particles dispersed throughout a liquid phase in which the particles are not soluble. The suspension is formulated to allow at least a reduction in dosing frequency as compared to that drug presented as a conventional dosage form (e.g., as a solution or a prompt drug-releasing, conventional solid dosage form). For example, a suspension of ion-exchange resin constituents or microbeads.

In embodiments, pharmaceutical compositions described herein are suitable for parenteral administration, including, e.g., intramuscular (i.m.), intravenous (i.v.), subcutaneous (s.c.), intraperitoneal (i.p.), or intrathecal (i.t.). Parenteral compositions must be sterile for administration by injection, infusion or implantation into the body and may be packaged in either single-dose or multi-dose containers. In embodiments, liquid pharmaceutical compositions for parenteral administration to a subject include an active substance, e.g., (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, in any of the respective amounts described above. In embodiments, the pharmaceutical compositions for parenteral administration are formulated as a total volume of about, e.g., 10 ml, 20 ml, 25 ml, 50 ml, 100 ml, 200 ml, 250 ml, or 500 ml. In embodiments, the compositions are contained in a bag, a glass vial, a plastic vial, or a bottle.

In embodiments, pharmaceutical compositions for parenteral administration include respective amounts described above for (1S,3S)-3-amino-4-(difluoromethylidene)cyclopentane carboxylic acid, or (S)-3-amino-4-(difluoromethylenyl)cyclopent-1-ene-1-carboxylic acid (KT-II-115), or a pharmaceutically acceptable salt of any of the preceding. In embodiments, pharmaceutical compositions for parenteral administration include about 0.05 mg to about 500 mg active substance, e.g., (1S,3S)-3-amino-4-(difluoromethylidene)cyclopentane-1-carboxylic acid, or (S)-3-amino (difluoromethylenyl)cyclopent-1-ene-1-carboxylic acid (KT-II-115), or a pharmaceutically acceptable salt of any of the preceding. In embodiments, pharmaceutical compositions for parenteral administration to a subject include an active substance, e.g., (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, at a respective concentration of about 0.005 mg/ml to about 500 mg/ml. In embodiments, the pharmaceutical composition for parenteral administration includes an active substance, e.g., (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, at a respective concentration of, e.g., about 0.05 mg/ml to about 50 mg/ml, about 0.1 mg/ml to about 50 mg/ml, about 0.1 mg/ml to about 10 mg/ml, about 0.05 mg/ml to about 25 mg/ml, about 0.05 mg/ml to about 10 mg/ml, about 0.05 mg/ml to about 5 mg/ml, or about 0.05 mg/ml to about 1 mg/ml. In embodiments, the pharmaceutical composition for parenteral administration includes an active substance, e.g., (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, at a respective concentration of, e.g., about 0.05 mg/ml to about 15 mg/ml, about 0.5 mg/ml to about 10 mg/ml, about 0.25 mg/ml to about 5 mg/ml, about 0.5 mg/ml to about 7 mg/ml, about 1 mg/ml to about 10 mg/ml, about 5 mg/ml to about 10 mg/ml, or about 5 mg/ml to about 15 mg/ml.

In embodiments, a pharmaceutical composition for parenteral administration is provided wherein the pharmaceutical composition is stable for at least six months. In embodiments, the pharmaceutical compositions for parenteral administration exhibit no more than about 5% decrease in active substance, e.g., (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, e.g., 3 months or 6 months. In embodiments, the amount of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, degrades at no more than about, e.g., 2.5%, 1%, 0.5% or 0.1%. In embodiments, the degradation is less than about, e.g., 5%, 2.5%, 1%, 0.5%, 0.25%, 0.1%, for at least six months.

In embodiments, pharmaceutical compositions for parenteral administration are provided wherein the pharmaceutical composition remains soluble. In embodiments, pharmaceutical compositions for parenteral administration are provided that are stable, soluble, local site compatible and/or ready-to-use. In embodiments, the pharmaceutical compositions herein are ready-to-use for direct administration to a subject in need thereof.

The pharmaceutical compositions for parenteral administration provided herein may include one or more excipients, e.g., solvents, solubility enhancers, suspending agents, buffering agents, isotonicity agents, stabilizers or antimicrobial preservatives. When used, the excipients of the parenteral compositions will not adversely affect the stability, bioavailability, safety, and/or efficacy of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, used in the composition. Thus, parenteral compositions are provided wherein there is no incompatibility between any of the components of the dosage form.

In embodiments, parenteral compositions including (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, include a stabilizing amount of at least one excipient. For example, excipients may be selected from the group consisting of buffering agents, solubilizing agents, tonicity agents, antioxidants, chelating agents, antimicrobial agents, and preservative. One skilled in the art will appreciate that an excipient may have more than one function and be classified in one or more defined group.

In embodiments, parenteral compositions including (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, and an excipient wherein the excipient is present at a weight percent (w/v) of less than about, e.g., 10%, 5%, 2.5%, 1%, or 0.5%. In embodiments, the excipient is present at a weight percent between about, e.g., 1.0% to 10%, 10% to 25%, 15% to 35%, 0.5% to 5%, 0.001% to 1%, 0.01% to 1%, 0.1% to 1%, or 0.5% to 1%. In embodiments, the excipient is present at a weight percent between about, e.g., 0.001% to 1%, 0.01% to 1%, 1.0% to 5%, 10% to 15%, or 1% to 15%.

In embodiments, parenteral compositions may be administered as needed, e.g., once, twice, thrice or four or more times daily, or continuously depending on the subject's needs.

In embodiments, parenteral compositions of an active substance, e.g., (1S,3S)-3-amino (difluoromethylidene)cyclopentane-1-carboxylic acid, or (S)-3-amino (difluoromethylenyl)cyclopent-1-ene-1-carboxylic acid (KT-II-115), or a pharmaceutically acceptable salt of any of the preceding, are provided, wherein the pH of the composition is between about 4.0 to about 8.0. In embodiments, the pH of the compositions is between, e.g., about 5.0 to about 8.0, about 6.0 to about 8.0, about 6.5 to about 8.0. In embodiments, the pH of the compositions is between, e.g., about 6.5 to about 7.5, about 7.0 to about 7.8, about 7.2 to about 7.8, or about 7.3 to about 7.6. In embodiments, the pH of the aqueous solution is, e.g., about 6.8, about 7.0, about 7.2, about 7.4, about 7.6, about 7.7, about 7.8, about 8.0, about 8.2, about 8.4, or about 8.6.

In embodiments, provided herein are methods of treating PWS or a seizure disorder including administering to a subject in need thereof a pharmaceutical composition including an active substance, e.g., one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, in a respective amount described herein, wherein the composition provides an in vivo plasma profile having a $C_{max}$ less than about 800 ng/ml. In embodiments, the composition provides improvement for more than 6 hours after administration to the subject.

In embodiments, pharmaceutical compositions including one or both of (1S,3S)-3-amino-4-(difluoromethylidene)cyclopentane-1-carboxylic acid, or(S)-3-amino-4-(difluoromethylenyl)cyclopent-1-ene-1-carboxylic acid (KT-II-115), or a pharmaceutically acceptable salt of any of the preceding, provide an in vivo plasma profile having a $C_{max}$ less than about, e.g., 2000 ng/ml, 1000 ng/ml, 850 ng/ml, 800 ng/ml, 750 ng/ml, 700 ng/ml, 650 ng/ml, 600 ng/ml, 550 ng/ml, 450 ng/ml, 400 ng/ml 350 ng/ml, or 300 ng/ml and wherein the composition provides improvement of next day functioning of the subject. In embodiments, the pharmaceutical composition provides an in vivo plasma profile having a $C_{max}$ less than about, e.g., 250 ng/ml, 200 ng/ml 150 ng/ml, or 100 ng/ml and wherein the composition provides improvement of next day functioning of the subject. In embodiments, the pharmaceutical composition provides improvement in one or more symptoms of a disorder herein for more than 6 hours after administration.

In embodiments, provided herein are methods of treating PWS or a seizure disorder including administering to a subject in need thereof a pharmaceutical composition containing one or both of (1S,3S)-3-amino-4-(difluoromethylidene)cyclopentane-1-carboxylic acid, or (S)-3-amino (difluoromethylenyl)cyclopent-1-ene-1-carboxylic acid (KT-II-115), or a pharmaceutically acceptable salt of any of the preceding, wherein the composition provides a consistent in vivo plasma profile having a $AUC_{0-\infty}$ of less than about 900 ng·hr/ml. In embodiments, the pharmaceutical composition provides improvement in next day functioning of the subject. In embodiments, the compositions provide an in vivo plasma profile having a $AUC_{0-\infty}$ of less than about, e.g., 850 ng·hr/ml, 800 ng·hr/ml, 750 ng·hr/ml, or 700 ng·hr/ml and wherein the pharmaceutical composition provides improvement of next day functioning of the subject. In embodiments, the composition provides improvement in one or more symptoms of a disorder herein for more than 6 hours after administration.

In embodiments, provided herein are methods of treating PWS or a seizure disorder including administering to a subject in need thereof a pharmaceutical composition comprising an active substance, e.g., one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, wherein the pharmaceutical composition provides an in vivo plasma profile having a $AUC_{0\infty}$ of less than about, e.g., 650 ng·hr/ml, 600 ng·hr/ml, 550 ng·hr/ml, 500 ng·hr/ml, or 450 ng·hr/ml. In embodiments, the composition provides an in vivo plasma profile having a $AUC_{0\infty}$ of less than about, e.g., 400 ng·hr/ml, 350 ng·hr/ml, 300 ng·hr/ml, 250 ng·hr/ml, or 200 ng·hr/ml. In embodiments, the pharmaceutical composition provides an in vivo plasma profile having a $AUC_{0\infty}$ of less than about, e.g., 150 ng·hr/ml, 100 ng·hr/ml, 75 ng·hr/ml, or 50 ng·hr/ml. In embodiments, the pharmaceutical composition provides improvement of next day functioning of the subject after administration for more than, e.g., 4 hours, 6 hours, 8 hours, 10 hours, or 12 hours, after administration of the composition to the subject.

In embodiments, provided herein are methods of treating PWS or a seizure disorder including administering to a subject in need thereof a first pharmaceutical composition including one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, and a second pharmaceutical composition including one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding.

In embodiments, the second pharmaceutical composition provides an in vivo plasma profile having a mean $AUC_{0\infty}$ which is about the same as the mean $AUC_{0\infty}$ of the first pharmaceutical composition. In embodiments, the second pharmaceutical composition provides an in vivo plasma profile having a mean $AUC_{0\infty}$ of at least about 20% less than the first pharmaceutical composition. In embodiments, provided herein are methods of treating PWS or a seizure disorder including administering to a subject in need thereof a first pharmaceutical composition including one or both of (1S,3S)-3-amino-4-(difluoromethylidene)cyclopentane-1-carboxylic acid, or (S)-3-amino (difluoromethylenyl)cyclopent-1-ene-1-carboxylic acid (KT-II-115), or a pharmaceutically acceptable salt of any of the preceding, and a second pharmaceutical composition including one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, wherein the second pharmaceutical composition provides a stable in vivo plasma profile having a mean $AUC_{0\infty}$ of at least about, e.g., 25%, 30%, 35%, 40%, 45% or 50% less than the first pharmaceutical composition. In embodiments, the compositions provide improvement of next day functioning of the subject. For example, the pharmaceutical compositions may provide improvement in one or more symptoms for more than about, e.g., 6 hours, 8 hours, 10 hours, 12 hours, 14 hours, 16 hours, 18 hours, 20 hours, 22 hours or 24 hours after administration of the first and/or second pharmaceutical composition.

In embodiments, provided herein are methods of treating PWS or a seizure disorder including administering to a subject in need thereof a first pharmaceutical composition including one or both (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, and a second pharmaceutical composition including one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, wherein the second pharmaceutical composition provides an in vivo plasma profile having a mean $AUC_{0\infty}$ of less than about 900 ng·hr/ml. In embodiments, the second pharmaceutical composition provides an in vivo plasma profile having a $AUC_{0\infty}$ of less than about, e.g., 800 ng·hr/ml, 750 ng·hr/ml, 700 ng·hr/ml, 650 ng·hr/ml, or 600 ng·hr/ml. In embodiments, the second pharmaceutical composition provides an in vivo plasma profile having a $AUC_{0\infty}$ of less than about, e.g., 550 ng·hr/ml, 500 ng·hr/ml, 450 ng·hr/ml, 400 ng·hr/ml, or 350 ng·hr/ml. In embodiments, the second pharmaceutical composition provides an in vivo plasma profile having a $AUC_{0\infty}$ of less than about, e.g., 300 ng·hr/ml, 250 ng·hr/ml, 200 ng·hr/ml, 150 ng·hr/ml, or 100 ng·hr/ml. In embodiments, the first and second pharmaceutical composition are administered wherein the compositions provide improvement of next day functioning of the subject. In embodiments, the first pharmaceutical composition provides improvement in one or more symptom for more than, e.g., 6 hours, 8 hours, 10 hours, 12 hours, 14 hours, 16 hours, 18 hours, 20 hours, 22 hours or 24 hours after administration of the first pharmaceutical composition.

In embodiments, provided herein are methods of treating PWS or a seizure disorder including administering to a subject in need thereof a first pharmaceutical composition including one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, and a second pharmaceutical composition including one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, wherein the first composition provides an in vivo plasma profile with a $C_{max}$ that is more than about 50% greater than the $C_{max}$ provided by the administration of the second pharmaceutical composition. As used herein the $C_{max}$ provided by the administration of the second pharmaceutical composition may or may not include the plasma profile contribution of the first pharmaceutical composition. In embodiments, the administration of the second pharmaceutical composition does not include the plasma profile contribution of the first pharmaceutical composition. In embodiments, the first composition provides an in vivo plasma profile having a $C_{max}$ that is more than about e.g., 60%, 70%, 80%, or 90% greater than the $C_{max}$ provided by the administration of the second pharmaceutical composition.

In embodiments, the $T_{max}$ of the first pharmaceutical composition is less than 3 hours. In embodiments, the $T_{max}$ of the first pharmaceutical composition is less than 2.5 hours. In embodiments, the $T_{max}$ of the first pharmaceutical composition is less than 2 hours. In embodiments, the $T_{max}$ of the first pharmaceutical composition is less than 1.5 hours. In embodiments, the $T_{max}$ of the first pharmaceutical composition is less than 1 hour. In embodiments, the $T_{max}$ of the first pharmaceutical composition is less than 0.5 hour. In embodiments, the $T_{max}$ of the first pharmaceutical composition is less than 0.25 hour. In embodiments, the $T_{max}$ of the second pharmaceutical composition is less than 3 hours. In embodiments, the $T_{max}$ of the second pharmaceutical composition is less than 2.5 hours. In embodiments, the $T_{max}$ of the second pharmaceutical composition is less than 2 hours. In embodiments, the $T_{max}$ of the second pharmaceutical composition is less than 1.5 hours. In embodiments, the $T_{max}$ of the second pharmaceutical composition is less than 1 hour. In embodiments, the $T_{max}$ of the second pharmaceutical composition is less than 0.5 hour. In embodiments, the $T_{max}$ of the second pharmaceutical composition is less than 0.25 hour.

In embodiments, the first pharmaceutical composition provides a dissolution of at least about 80% within the first 20 minutes of administration to a subject in need thereof. In embodiments, the first pharmaceutical composition provides a dissolution of at least about, e.g., 85%, 90% or 95% within the first 20 minutes of administration to a subject in need thereof. In embodiments, the first pharmaceutical composition provides a dissolution of at least 80% within the first 10 minutes of administration to a subject in need thereof.

In embodiments, administration of the first and second pharmaceutical compositions may be simultaneous or separated by an interval of time to achieve long-term improvement in at least one symptom. In embodiments, the first and second pharmaceutical composition may be administered 1, 2, 3, 4, 5, 6, 7, 8, 9, 10, 11, or 12 hours apart. In embodiments the first and second pharmaceutical composition may be administered 12 hours apart. In embodiments, the first and second pharmaceutical compositions may administered within, e.g., 15 minutes, 30 minutes, 1 hour, 2 hours, 6 hours, 12 hours, 18 hours, 24 hours, etc. In embodiments, the first and second pharmaceutical compositions may administered separated by at least, e.g., 15 minutes, 30 minutes, 1 hour, 2 hours, 12 hours, 18 hours, 24 hours, etc. In embodiments, improvement in at least one symptom of PWS or seizure disorder for more than 8 hours after administration to the subject is provided. In embodiments, improvement for more than about, e.g., 10 hours, 12 hours, 15 hours, 18 hours, 20 hours, 24 hours, 30 hours, 36 hours, 42 hours or 48 hours after administration to the subject is provided.

In embodiments, the administration of the first and second pharmaceutical composition may provide a synergistic effect to improve at least one symptom of PWS or a seizure disorder.

In embodiments, provided herein are methods of treating PWS or a seizure including administering to a subject in need thereof a first pharmaceutical dosage including a sub-therapeutic amount of one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding. In embodiments, treating PWS or a seizure disorder includes administering to a subject in need thereof a first pharmaceutical dosage including a sub-therapeutic amount of one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, wherein the composition provides improvement in one or more symptoms of the disorder for more than 6 hours after administration.

In embodiments, the first and/or the second pharmaceutical compositions contain sub-therapeutic dosages. A sub-therapeutic dosage is an amount of active substance, e.g., one or both of (1S,3S)-3-amino-4-(difluoromethylidene)cyclopentane-1-carboxylic acid, or (S)-3-amino (difluoromethylenyl)cyclopent-1-ene-1-carboxylic acid (KT-II-115), or a pharmaceutically acceptable salt of any of the preceding, that is less than the amount typically required for a therapeutic effect. In embodiments, a sub-therapeutic dosage is an amount of one or both of (1S,3S)-3-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, that alone may not provide improvement in at least one symptom of PWS or a seizure disorder but is sufficient to maintain such improvement. In embodiments, the methods provide administering a first pharmaceutical composition that provides improvement in at least one symptom of PWS or a seizure disorder and a second composition that maintains the improvement. In embodiments, the second composition contains a sub-therapeutic dose of one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding. In embodiments, after administration of the first pharmaceutical composition, the second pharmaceutical composition may provide a synergistic effect to improve at least one symptom of PWS or a seizure disorder. In embodiments, the second pharmaceutical composition may provide a synergistic effect to improve at least one symptom of PWS or seizure disorder.

In embodiments, provided herein are methods of treating PWS or a seizure disorder including administering to a subject in need thereof a first pharmaceutical composition including a first pharmaceutical dosage of, e.g., one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, wherein the first pharmaceutical dosage provides improvement for more than 6 hours after administration, and a second pharmaceutical composition including a sub-therapeutic dosage of one or both of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115 or a pharmaceutically acceptable salt of any of the preceding.

In embodiments, the first or the second pharmaceutical composition are provided to the subject once in the evening and once in the morning. In embodiments, the total amount of one or both of (1S,3S)-3-amino-4-(difluoromethylidene) cyclopentane-1-carboxylic acid, or (S)-3-amino (difluoromethylenyl)cyclopent-1-ene-1-carboxylic acid (KT-II-115), or a pharmaceutically acceptable salt of any of the preceding, administered to a subject in a 24-hour period is any of the respective amounts described herein.

In embodiments, the first and/or the second pharmaceutical compositions may be provided with conventional release or modified release profiles. The first and second pharmaceutical compositions may be provided at the same time or separated by an interval of time, e.g., 1 hour, 2 hours, 3 hours, 4 hours, 5 hours, 6 hours, 12 hours, etc. In embodiments, the first and the second pharmaceutical compositions may be provided with different drug release profiles to create a two-phase release profile. For example, the first pharmaceutical composition may be provided with an immediate release profile, e.g., ODDF, parenteral, etc., and the second pharmaceutical composition may provide an extended release profile. In embodiments, one or both of the first and second pharmaceutical compositions may be provided with an extended release or delayed release profile. Such compositions may be provided as pulsatile formulations, multilayer tablets or capsules containing tablets, beads, granules, etc. In embodiments, the first pharmaceutical composition is an immediate release composition. In embodiments, the second pharmaceutical composition is an immediate release composition. In embodiments, the first and second pharmaceutical compositions are provided as separate immediate release compositions, e.g., film, tablets or capsules. In embodiments the first and second pharmaceutical compositions are provided 12 hours apart.

It should be understood that respective dosage amounts of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, that are provided herein are applicable to all the dosage forms described herein including conventional dosage forms, modified dosage forms, the first and second pharmaceutical compositions, as well as the parenteral formulations described herein. Those skilled in the art will determine appropriate amounts depending on criteria such as dosage form, route of administration, subject tolerance, efficacy, therapeutic goal and therapeutic benefit, among other pharmaceutically acceptable criteria.

Combination therapies utilizing one or both (1S,3S)-3-amino-4-(difluoromethylidene)cyclopentane-1-carboxylic acid, or (S)-3-amino (difluoromethylenyl)cyclopent-1-ene-1-carboxylic acid (KT-II-115), or a pharmaceutically acceptable salt of any of the preceding, can include administration of the active agents together in the same admixture, or in separate admixtures. In embodiments, the pharmaceutical composition can includes two, three, or more active agents. In embodiments, the combinations result in a more than additive effect on the treatment of the disease or disorder. Thus, treatment is provided for PWS or a seizure disorder with a combination of agents that combined, may provide a synergistic effect that enhances efficacy.

In embodiments, a co-therapy of (1S,3S)-3-amino-4-(difluoromethylidene)cyclopentane-1-carboxylic acid, and (S)-3-amino-4-(difluoromethylenyl)cyclopent-1-ene-1-carboxylic acid (KT-II-115), or a pharmaceutically acceptable salt of any of the preceding, is effective to reduce frequency or severity of symptoms in the subject greater than any of the compounds administered alone. In embodiments, the co-therapy produces a more than additive result compared to compounds administered individually.

In embodiments, the subject may be started at a low dose and the dosage is escalated. In this manner, it can be determined if the drug is well tolerated in the subject. Dosages can be lower for children than for adults.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and/or up to 1% of a given value. Alternatively, particularly with respect to biological systems or processes, the term can mean within an order of magnitude, preferably within 5-fold, and more preferably within 2-fold, of a value.

"Improvement" refers to the treatment of PWS or seizure disorders such as epilepsy, epilepsy with generalized tonic-clonic seizures, epilepsy with myoclonic absences, frontal lobe epilepsy, temporal lobe epilepsy, Landau-Kleffner Syndrome, Rasmussen's syndrome, Dravet syndrome, Doose syndrome, CDKL5 disorder, infantile spasms (West syndrome), juvenile myoclonic epilepsy (JME), vaccine-related encephalopathy, intractable childhood epilepsy (ICE), Lennox-Gastaut syndrome (LGS), Rett syndrome, Ohtahara syndrome, childhood absence epilepsy, essential tremor, acute repetitive seizures, benign rolandic epilepsy, status epilepticus, refractory status epilepticus, super-refractory status epilepticus (SRSE), PCDH19 pediatric epilepsy, abnormal EEG signature, drug withdrawal induced seizures, alcohol withdrawal induced seizures, increased seizure activity or breakthrough seizures (also called serial or cluster seizures), measured relative to at least one symptom of the foregoing disorders.

"Improvement in next day functioning" or "wherein there is improvement in next day functioning" refers to improvement after waking from an overnight sleep period wherein the beneficial effect of administration of (1S,3S)-3-amino-4-(difluoromethylidene)cyclopentane-1-carboxylic acid, or (S)-3-amino-4-(difluoromethylenyl)cyclopent-1-ene-1-carboxylic acid (KT-II-115), or a pharmaceutically acceptable salt of any of the preceding, applies to at least one symptom of a syndrome or disorder herein and is discernable, either subjectively by a subject or objectively by an observer, for a period of time, e.g., 2 hours, 3 hours, 4 hours, 5 hours, 6 hours, 12 hours, 24 hours, etc. after waking.

"PK" refers to the pharmacokinetic profile. $C_{max}$ is defined as the highest plasma drug concentration estimated during an experiment (ng/ml). $T_{max}$ is defined as the time when $C_{max}$ is estimated (min). $AUC_{0-\infty}$ is the total area under the plasma drug concentration-time curve, from drug administration until the drug is eliminated (ng·hr/ml or µg·hr/ml). The area under the curve is governed by clearance. Clearance is defined as the volume of blood or plasma that is totally cleared of its content of drug per unit time (ml/min).

"Treating", "treatment" or "treat" can refer to the following: alleviating or delaying the appearance of clinical symptoms of a disease or condition in a subject that may be afflicted with or predisposed to the disease or condition, but does not yet experience or display clinical or subclinical symptoms of the disease or condition. In certain embodiments, "treating", "treat" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating", "treat" or "treatment" also refers to inhibiting the disease or condition, e.g., arresting or reducing its development or at least one clinical or subclinical symptom thereof. "Treating", "treat" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic (curative) treatment are two separate embodiments of the disclosure herein.

"Pharmaceutically acceptable" refers to molecular entities and compositions that are "generally regarded as safe", e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Effective amount" or "therapeutically effective amount", previously referred to, can also mean a dosage sufficient to alleviate one or more symptoms of a syndrome, disorder, disease, or condition being treated, or to otherwise provide a desired pharmacological and/or physiologic effect. "Effective amount" or "therapeutically effective amount" may be used interchangeably herein.

"Co-administered with", "administered in combination with", "a combination of", "in combination with" or "administered along with" may be used interchangeably and mean that two or more agents are administered in the course of therapy. The agents may be administered together at the same time or separately in spaced apart intervals. The agents may be administered in a single dosage form or in separate dosage forms.

"Subject in need thereof" may include individuals that have been diagnosed with PWS or a seizure disorder such as epilepsy, epilepsy with generalized tonic-clonic seizures, epilepsy with myoclonic absences, frontal lobe epilepsy, temporal lobe epilepsy, Landau-Kleffner Syndrome, Rasmussen's syndrome, Dravet syndrome, Doose syndrome, CDKL5 disorder, infantile spasms (West syndrome), juvenile myoclonic epilepsy (JME), vaccine-related encephalopathy, intractable childhood epilepsy (ICE), Lennox-Gastaut syndrome (LGS), Rett syndrome, Ohtahara syndrome, CDKL5 disorder, childhood absence epilepsy, essential tremor, acute repetitive seizures, benign rolandic epilepsy, status epilepticus, refractory status epilepticus, super-refractory status epilepticus (SRSE), PCDH19 pediatric epilepsy, abnormal EEG signature, drug withdrawal induced seizures, alcohol withdrawal induced seizures, increased seizure activity or breakthrough seizures (also called serial or cluster seizures). The methods may be provided to any individual including, e.g., wherein the subject is a neonate, infant, a pediatric subject (6 months to 12 years), an adolescent subject (age 12-18 years) or an adult (over 18 years). Subjects include mammals. "Subject" and "patient" are used interchangeably herein.

"Prodrug" refers to a pharmacological substance (drug) that is administered to a subject in an inactive (or significantly less active) form. Once administered, the prodrug is metabolized in the body (in vivo) into a compound having the desired pharmacological activity.

"Analog" and "Derivative" may be used interchangeably and refer to a compound that possesses the same core as the parent compound, but may differ from the parent compound in bond order, the absence or presence of one or more atoms and/or groups of atoms, and combinations thereof. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

The term "pharmaceutically acceptable salt", as used herein, refers to derivatives of the compounds defined herein, wherein the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include but are not limited to those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts. The pharmaceutically acceptable salts can be synthesized from the parent compound, which contains a basic or acidic moiety, by conventional chemical methods.

EXAMPLES

The examples provided herein are included solely for augmenting the disclosure herein and should not be considered to be limiting in any respect.

Example 1

Prospective Assessment of the Safety and Efficacy of (1S,3S)-3-amino-4-(difluoromethylidene)cyclopentane-1-carboxylic Acid in Ghrelin Suppression in Individuals with Prader-Willi Syndrome The purpose of this study is to evaluate the effect of (1S,3S)-3-amino-4-(difluoromethylidene)cyclopentane-1-carboxylic acid on levels of ghrelin, hunger, and body weight in people with Prader-Willi syndrome. This study will be a multi-center, randomized, placebo-controlled, double blind trial in which subjects meeting entrance criteria will be randomly assigned to receive placebo or active drug. Enrolled subjects will have diagnosis of PWS confirmed by chromosome analysis (i.e. interstitial deletion of paternally-derived chromosome 15Q, uniparental maternal disomy or other chromosome 15 abnormalities), be 18 years and older, and have free T4, TSH values in the normal range (with or without thyroxine replacement). Subjects with confirmed hypogonadism who are corrected with adequate doses of sex steroid replacement, will have been treated for at least 6 months prior to entry and have no change in dosages over the study period. Subjects with confirmed growth hormone deficiency who are corrected with adequate doses of replacement, will have been treated for at least 6 months prior to entry and have no change in dosages over the study period.

After baseline tests, subjects will be administered (1S,3S)-3-amino-4-(difluoromethylidene)cyclopentane-1-carboxylic acid or placebo for 6 months. At the end of this initial 6-month treatment period and a 4-month washout period, study subjects will then crossover to receive the alternative therapy (placebo or (1S,3S)-3-amino-4-(difluoromethylidene)cyclopentane-1-carboxylic acid for an additional 6 months. Subjects will be followed for 16 months total at scheduled visits: 0, 2, 6, 10, 12, and 16 months. During each of these visits, testing will include measuring how well glucose (sugar) is processed, how much energy is burned off as heat, their amount of body fat, levels of the hormone ghrelin, and how much food is eaten at a meal. During these study periods participants will return monthly for physical examination and blood draw to check liver enzymes. Primary outcome measures are ghrelin levels (change from baseline to 6 months), appetite (change from baseline to 6 months), and body weight (change from baseline to 6 months). Secondary outcome measures are hormone levels (change from baseline to 6 months), body composition (change from baseline to 6 months), energy expenditure (change from baseline to 6 months), and glucose metabolism (change from baseline to 6 months).

Example 2

Prospective Assessment of the Effect of (S)-3-amino-4-(difluoromethylenyl)cyclopent-1-ene-1-carboxylic Acid on Weight Gain and Body Composition in Adults with Prader-Willi Syndrome The purpose of this study will be to evaluate the effect of (S)-3-amino-4-(difluoromethylenyl)cyclopent-1-ene-1-carboxylic acid (KT-II-115) on the appetite, body weight, body fat and growth hormone level of subjects with PWS. This will be a double blind placebo controlled clinical trial involving a total of 18 young adults aged 18 to 35 years with PWS. Subjects will be selected if they have Prader Willi syndrome previously confirmed by standard genetic testing (the DNA methylation test) or meet the clinical diagnostic criteria as follows: the presence of at least four of the six principal characteristics of PWS syndrome including 1) infantile hypotonia, 2) abnormal pubertal development, 3) obesity after early infancy, 4) dysfunctional central nervous system performance, 5) dysmorphic facial features, and 6) short stature. In addition, they must have one or more of the following characteristics commonly associated with PWS: 1) small hands and feet, 2) skin problems, 3) behavioral problems related to food, and 4) decreased pain sensitivity. Subjects must have a BMI of at least 30 or more. Subjects will be divided in to the two groups of control and intervention, and treated with either placebo (inactive drug), or (S)-3-amino-4-(difluoromethylenyl)cyclopent-1-ene-1-carboxylic acid (KT-II-115) for a total duration of 6 months. Body weight, fat distribution, objective and subjective assessment of the hunger, fasting blood sample for measurement of ghrelin and leptin, serum lipids, IGF-1 (growth hormone related protein), insulin and glucose concentrations will be measured upon enrollment, at 3 months, and at the end of the study. The proportion of body fat to muscle will be determined using a radiological technique, whole body dual-energy x-ray absorptiometry (DEXA) scan, and also by measurement of skin fold thickness, waist and hip circumference at the enrollment prior to the intervention, and at the end of the study.

Example 3

Prospective Assessment of the Effect of (S)-3-amino-4-(difluoromethylenyl)cyclopent-1-ene carboxylic Acid (KT-II-115) Therapy on Developmental, Nutritional and Hormonal Regulation of Ghrelin in Children and Young Adults With Prader-Willi Syndrome The purpose of this study is to investigate, over a 6 month period, the effect of (S)-3-amino-4-(difluoromethylenyl)cyclopent-1-ene-1-carboxylic acid therapy on food intake, sense of hunger, body weight, body composition, efficiency of burning calories, biomarkers of weight regulation and growth hormone markers in children and young Adults with PWS. This will be a double blind placebo controlled clinical trial involving subjects with a diagnosis of PWS confirmed by chromosome analysis, ages 5 years to 21 years, BMI for age greater-than or equal to 85th percentile, and free T4, thyroid stimulating hormone (TSH) values in the normal range (either endogenous or with thyroxine replacement).

Primary outcome measures are number of participants showing a decrease in fasting total ghrelin from baseline to 6 months of treatment with (S)-3-amino-4-(difluoromethylenyl)cyclopent-1-ene-1-carboxylic acid or placebo, number of participants with a decrease in weight from baseline to 6 months of (S)-3-amino-4-(difluoromethylenyl)cyclopent-1-ene-1-carboxylic acid or placebo therapy, number of participants with decreased BMI z-score from baseline to 6 months of (S)-3-amino-4-(difluoromethylenyl)cyclopent-1-ene-1-carboxylic acid or placebo therapy, number of participants with decreased skin-fold measurements from baseline to 6 months of (S)-3-amino-4-(difluoromethylenyl)cyclopent-1-ene-1-carboxylic acid or placebo therapy, number of participants with decrease in hunger and food intake measured by hunger and hyperphagia by questionnaires and parent-reported 72-hour food recall from baseline to 6 months of (S)-3-amino-4-(difluoromethylenyl)cyclopent-1-ene-1-carboxylic acid or placebo therapy. Multiple questionnaires consisting of a battery of free text answer questions and food diaries are combined in order to make a behavioral assessment of the participants food state of hunger and food intake. There is no defined scale for this assessment. Each participants' responses and parent responses are combined. Additional primary outcome measures are number of participants with improved insulin regulation from baseline to 6 months of (S)-3-amino-4-(difluoromethylenyl)cyclopent-1-ene-1-carboxylic acid or placebo therapy. Insulin regulation will be measured by immunochemiluminescent assay, number of participants with improved adiponectin regulation from baseline to 6 months of (S)-3-amino (difluoromethylenyl)cyclopent-1-ene-1-carboxylic acid or placebo therapy, number of participants with improved Leptin regulation from baseline to 6 months of (S)-3-amino (difluoromethylenyl)cyclopent-1-ene-1-carboxylic acid or placebo therapy, and number of participants with improved Peptide YY (PYY) regulation from baseline to 6 months of (S)-3-amino-4-(difluoromethylenyl)cyclopent-1-ene-1-carboxylic acid or placebo therapy. Secondary outcome measures are number of participants with decreased body-composition as measured by air displacement plethysmography (BOD POD® body composition tracking system) from baseline to 6 months of (S)-3-amino-4-(difluoromethylenyl)cyclopent-1-ene-1-carboxylic acid or placebo therapy, number of participants with decreased body-composition as measured by dual energy X-ray absorptiometry (DEXA) scan from baseline to 6 months of (S)-3-amino-4-(difluoromethylenyl)cyclopent-1-ene-1-carboxylic acid or placebo therapy measured at months 0, 3, and 6, and resting energy expenditure as measured by indirect calorimetry at months 0, 3 and 6.

Example 4

Prospective Assessment of the Efficacy of (S)-3-amino-4-(difluoromethylenyl)cyclopent-1-ene-1-carboxylic Acid in Pediatric Subjects with Status Epilepticus This study is designed to determine whether with (S)-3-amino-4-(difluoromethylenyl)cyclopent-1-ene-1-carboxylic acid leads to an improvement in one or more symptoms of status epilepticus. Epilepsy is among the most common serious neurologic disorders in childhood. Medicines with novel actions of mechanisms of action are needed to try to address the unmet clinical need for seizure control in subjects with status epilepticus. In addition, the purpose of this study is to evaluate the safety and tolerability of (S)-3-amino-4-(difluoromethylenyl)cyclopent-1-ene-1-carboxylic acid as treatment in subjects with status epilepticus.

(S)-3-amino-4-(difluoromethylenyl)cyclopent-1-ene-1-carboxylic acid or a pharmaceutically acceptable salt thereof such as hydrochloric will be administered intravenously to pediatric subjects (3 months to 16 years) in amounts ranging from 0.25, 0.5, 1, 1.5, 2, 2.5, 3, 4, 5, 6, 7, 8, 9, and 10 mg as 50 mL short-term infusion solution intravenously (IV) within 15 minutes (infusion rate 200 mL/h). Subjects whose seizure does not stop or recurs within 10 minutes after the initial dose may receive the same amount of (S)-3-amino-4-(difluoromethylenyl)cyclopent-1-ene-1-carboxylic acid injection no earlier than 10 minutes following the initial dose. Subjects whose seizure stops within 10 minutes after the initial dose, but recurs thereafter (within 12 hours) may receive the same amount of (S) amino-4-(difluoromethylenyl)cyclopent-1-ene-1-carboxylic acid injection; a total of 2 doses will be permitted in this study.

Inclusion Criteria:
  Subjects with status epilepticus or repetitive status epilepticus/cluster seizure who have seizures that can be evaluated by investigator's visual observations based on motor symptoms or who have seizures that can be evaluated by EEG.
  Subjects with status epilepticus accompanied by generalized seizure, partial seizure or secondarily generalized seizure lasting 5 minutes or longer
  Subjects with repetitive status epilepticus/cluster seizure accompanied by not less than 3 consecutive episodes of generalized seizure, partial seizure or secondarily generalized seizure in 1 hour.
  Subjects not younger than 3 months (either gender is eligible for the study)

Primary Outcome Measures:
  Percentage of Participants With Clinical Benefit [Time Frame: 30 minutes]
  Percent of participants whose initial seizure stopped within 10 minutes after initial dose and who continued seizure-free for at least 30 minutes after the completion of initial dose (responder rate)

Secondary Outcome Measures:
  Percent of participants whose initial seizure stopped within 10 minutes after the administration of (S)-3-amino-4-(difluoromethylenyl)cyclopent-1-ene-1-carboxylic acid (either initial or second dose [in 10 to 30 minutes from the initial dose]) and who continued seizure-free for at least 30 minutes. [Time Frame: 1 hour]
  Percent of participants whose seizures stopped within 10 minutes after the administration of (S)-3-amino-4-(difluoromethylenyl)cyclopent-1-ene-1-carboxylic acid (only the initial dose) and who continued seizure-free for at least 12 hours post-dose. [Time Frame: 12 hours]
  Percent of participants whose seizures stopped within 10 minutes after the administration of (S)-3-amino-4-(difluoromethylenyl)cyclopent-1-ene-1-carboxylic acid (either initial or second dose [in 10 to 30 minutes from the initial dose]) and who continued seizure-free for at least 12 hours post-dose. [Time Frame: 12 hours]
  Percent of participants whose seizures stopped within 10 minutes after the administration of (S)-3-amino-4-(difluoromethylenyl)cyclopent-1-ene-1-carboxylic acid (only the initial dose) and who continued seizure-free for at least 24 hours post-dose. [Time Frame: 24 hours]
  Percent of participants whose seizures stopped within 10 minutes after the administration of (S)-3-amino-4-(difluoromethylenyl)cyclopent-1-ene-1-carboxylic acid (either initial or second dose [in 10 to 30 minutes from the initial dose]) and who continued seizure-free for at least 24 hours post-dose. [Time Frame: 24 hours]
  Time to resolution of seizures from the administration of (S)-3-amino-4-(difluoromethylenyl)cyclopent-1-ene-1-carboxylic acid (only the initial dose). [Time Frame: 24 hours]
  Time to resolution of seizures from the administration of (S)-3-amino-4-(difluoromethylenyl)cyclopent-1-ene-1-carboxylic acid (either initial or second dose). [Time Frame: 24 hours]
  Time to relapse from the resolution of seizures following the administration of (S)-3-amino-4-(difluoromethylenyl)cyclopent-1-ene-1-carboxylic acid (only the initial dose, within 24 hours). [Time Frame: 24 hours]
  Time to relapse from the resolution of seizures following the administration of (S)-3-amino-4-(difluoromethylenyl)cyclopent-1-ene-1-carboxylic acid (either initial or second dose, within 24 hours). [Time Frame: 24 hours]

Example 5

Prospective Assessment of the Use of (S)-3-amino-4-(difluoromethylenyl)cyclopent-1-ene-1-carboxylic Acid to Prevent Epilepsy in Infants with Tuberous Sclerosis Complex A multi-center, randomized, placebo-controlled, double-blind clinical trial. 80 infants with Tuberous Sclerosis Complex who are less than 6 months of age prior to the onset of their first seizure will be enrolled. Early identification of electroencephalography (EEG) biomarkers and early treatment versus delayed treatment with (S)-3-amino-4-(difluoromethylenyl)cyclopent-1-ene-1-carboxylic acid in infants with tuberous sclerosis complex (TSC) will be assessed for positive impact on developmental outcomes at 24 months of age. Early treatment should prevent or lower the risk of developing infantile spasms and refractory seizures. This preventative approach should result in more favorable long-term cognitive, behavioral, developmental and psychiatric outcomes and significantly improve overall quality of life.

Inclusion criteria are infants less than or equal to 6 months of age, no history of seizures or infantile spasms, or evidence of subclinical electrographic seizures on a previous video EEG, and meet genetic or clinical diagnostic criteria for TSC, the latter based on current recommendations for diagnostic evaluation, such as physical exam, neuroimaging, echocardiogram.

(S)-3-amino-4-(difluoromethylenyl)cyclopent-1-ene-1-carboxylic acid or placebo will be dosed according to body weight 1 mg to 50 mg/kg/day divided twice daily. Dosing will follow established recommended guidelines (1 mg/kg/day and increased as needed by 10 mg/kg/day every 3 days up to a maximum dose of 50 mg/kg/day, divided twice daily).

Subjects randomized to (S)-3-amino-4-(difluoromethylenyl)cyclopent-1-ene-1-carboxylic acid in Arm A will be treated with (S)-3-amino-4-(difluoromethylenyl)cyclopent-1-ene-1-carboxylic acid up to 50 mg/kg/day or placebo until 24 months of age or until they show evidence of clinical seizures or electrographic seizures on video EEG. If electrographic or clinical seizures occur while on study drug, they will transition into an Open label phase of the study (Arm B) and continue to be followed until 36 months of age. (S)-3-amino-4-(difluoromethylenyl)cyclopent-1-ene-1-carboxylic acid open label (Arm B) will be given for administration, dosed according to body weight 1 mg to 50 mg/kg/day divided twice daily. Dosing will follow established recommended guidelines (1 mg/kg/day and increased as needed by 10 mg/kg/day every 3 days up to a maximum dose of 50 mg/kg/day, divided twice daily).

Primary outcome measures: cognitive assessment scores on the Bayley Scales of Infant and Toddler Development at 24 months and Bayley Scales of Infant and Toddler Development at 24 months will be used for the data analysis and compare the developmental impact of early versus delayed treatment with (S)-3-amino-4-(difluoromethylenyl)cyclopent-1-ene-1-carboxylic acid.

Secondary outcome measures: 1. Evaluate the number of subjects that develop seizures when treated with (S)-3-amino-4-(difluoromethylenyl)cyclopent-1-ene-1-carboxylic acid as a seizure prevention, 2. Time to the subject's first clinical seizure will be measured for both subjects on placebo and (S)-3-amino-4-(difluoromethylenyl)cyclopent-1-ene-1-carboxylic acid, 3. The prevalence of drug resistant epilepsy, 4. Evaluate Vineland II scores and the impact of early versus late treatment with (S)-3-amino-4-(difluoromethylenyl)cyclopent-1-ene-1-carboxylic acid at 12, 24, and 36 months, 5. Evaluate ADOS2 scores and the impact of early versus late treatment at 24 and 36 months, 6. Number of subjects with (S)-3-amino-4-(difluoromethylenyl)cyclopent-1-ene-1-carboxylic acid related adverse events, severe adverse events as assessed by CTCAE v4.0 and risk evaluation and mitigation strategy (REMS) measures.

It should be understood that the examples and embodiments provided herein are exemplary examples embodiments. Those skilled in the art will envision various modifications of the examples and embodiments that are consistent with the scope of the disclosure herein. Such modifications are intended to be encompassed by the claims.

What is claimed is:

1. A method of treating tuberous sclerosis complex comprising administering to a subject with the tuberous sclerosis complex (S)-3-amino-4-(difluoromethylenyl)cyclopent-1-ene-1-carboxylic acid or a pharmaceutically acceptable salt thereof in an amount of from 0.01 mg to 750 mg.

2. The method of treating tuberous sclerosis complex according to claim 1, wherein the total amount of (S)-3-amino-4-(difluoromethylenyl)cyclopent-1-ene-1-carboxylic acid or a pharmaceutically acceptable salt thereof administered to the subject in a twenty-four hour period is between 1 mg and 500 mg.

3. The method of treating tuberous sclerosis complex according to claim 1, wherein the method provides improvement in at least one symptom selected from the group consisting of ataxia, gait impairment, speech impairment, vocalization, impaired cognition, abnormal motor activity, clinical seizure, subclinical seizure, hypotonia, hypertonia, drooling, mouthing behavior, aura, convulsions, repetitive movements, unusual sensations, simple focal seizures, complex focal seizures, generalized seizures, absences, tonic seizures, atonic seizures, myoclonic seizures, tonic clonic seizures, clonic seizures, frequency of seizures and severity of seizures.

4. The method of treating tuberous sclerosis complex according to claim 1, wherein the method provides improvement in at least one symptom selected from the group consisting of seizures, cognitive impairment, autism, gelastic seizures, involuntary laughter, interval irritability and depressed mood.

5. A method of treating tuberous sclerosis complex comprising administering (S)-3-amino-4-(difluoromethylenyl)cyclopent-1-ene-1-carboxylic acid or a pharmaceutically acceptable salt thereof to a subject in need thereof prior to the onset of clinical seizures after detection of abnormal EEG to reduce or prevent symptoms of the tuberous sclerosis complex.

6. The method of treating tuberous sclerosis complex according to claim 5, wherein the total amount of (S)-3-amino-4-(difluoromethylenyl)cyclopent-1-ene-1-carboxylic acid or a pharmaceutically acceptable salt thereof administered to the subject in a twenty-four hour period is between 1 mg and 500 mg.

7. A method of treating an abnormal EEG signature in a subject diagnosed with tuberous sclerosis complex comprising administering (S)-3-amino-4-(difluoromethylenyl)cyclopent-1-ene-1-carboxylic acid or a pharmaceutically acceptable salt thereof to the subject having the abnormal EEG signature.

* * * * *